(12) United States Patent
Kilcran et al.

(10) Patent No.: US 10,799,153 B2
(45) Date of Patent: Oct. 13, 2020

(54) PATIENT MOVEMENT AND INCONTINENCE NOTIFICATION SYSTEM

(71) Applicant: Parasol Medical LLC, Buffalo Grove, IL (US)

(72) Inventors: Michael D. Kilcran, Antioch, IL (US); Patrick E. Eddy, Allendale, MI (US); Jacob D. Stephens, Lowell, MI (US); Lucas W. Stephens, Lowell, MI (US); Daniel P. Kilcran, Libertyville, IL (US)

(73) Assignee: Parasol Medical LLC, Buffalo Grove, IL (US)

( * ) Notice: Subject to any disclaimer, the term of this patent is extended or adjusted under 35 U.S.C. 154(b) by 0 days.

(21) Appl. No.: 16/100,968

(22) Filed: Aug. 10, 2018

(65) Prior Publication Data

US 2019/0046081 A1 Feb. 14, 2019

Related U.S. Application Data

(60) Provisional application No. 62/649,088, filed on Mar. 28, 2018, provisional application No. 62/543,436, filed on Aug. 10, 2017.

(51) Int. Cl.
*G08B 23/00* (2006.01)
*A61B 5/11* (2006.01)
(Continued)

(52) U.S. Cl.
CPC ............ *A61B 5/1115* (2013.01); *A61B 5/002* (2013.01); *A61B 5/0022* (2013.01); *A61B 5/6808* (2013.01); *A61F 13/42* (2013.01); *G08B 5/36* (2013.01); *G08B 21/043* (2013.01); *G08B 21/0461* (2013.01); *G08B 21/20* (2013.01); *G08B 21/22* (2013.01); *G08B 25/10* (2013.01); *A61B 5/202* (2013.01); *A61B 5/6891* (2013.01); *A61B 5/6892* (2013.01); *A61B 5/6894* (2013.01); *A61B 5/746* (2013.01);
(Continued)

(58) Field of Classification Search
None
See application file for complete search history.

(56) References Cited

U.S. PATENT DOCUMENTS

| | | |
|---|---|---|
| 3,954,100 A | 5/1976 | Sem-Jacobsen |
| 4,551,028 A | 11/1985 | Rowen et al. |

(Continued)

FOREIGN PATENT DOCUMENTS

| | | |
|---|---|---|
| CN | 103617700 A | 3/2014 |
| EA | 018662 | 9/2013 |

(Continued)

OTHER PUBLICATIONS

Tabs Mobility Monitor User Instructions (Tabs Mobility Monitor Model #s 25222 and 25223), pp. 1-25, 2007.
(Continued)

*Primary Examiner* — Julie B Lieu
(74) *Attorney, Agent, or Firm* — Price Heneveld LLP

(57) ABSTRACT

A notification system is provided that provides notification of patient events such as movement and/or incontinence. The notification system provides for a plurality of different pressure sensor pads as well as an incontinence pad to be used in association with a single monitor.

13 Claims, 25 Drawing Sheets

(51) Int. Cl.
    *A61B 5/00*     (2006.01)
    *G08B 21/04*     (2006.01)
    *G08B 25/10*     (2006.01)
    *A61F 13/42*     (2006.01)
    *G08B 21/20*     (2006.01)
    *G08B 21/22*     (2006.01)
    *G08B 5/36*     (2006.01)
    *G08B 29/18*     (2006.01)
    *A61B 5/20*     (2006.01)

(52) U.S. Cl.
    CPC ....... *A61B 5/7465* (2013.01); *A61F 2013/424* (2013.01); *G08B 21/0415* (2013.01); *G08B 29/181* (2013.01)

(56) References Cited

U.S. PATENT DOCUMENTS

| | | |
|---|---|---|
| 4,865,844 A | 9/1989 | Blank et al. |
| 5,144,284 A | 9/1992 | Hammett |
| 5,342,583 A | 8/1994 | Son |
| 5,410,297 A | 4/1995 | Joseph et al. |
| 5,537,095 A | 7/1996 | Dick et al. |
| 5,654,694 A | 8/1997 | Newham |
| 5,844,488 A | 12/1998 | Musick |
| 6,078,261 A | 6/2000 | Davsko |
| 6,200,250 B1 | 3/2001 | Janszen |
| 6,283,938 B1 | 9/2001 | McConnell |
| 6,317,036 B1 | 11/2001 | Popat et al. |
| 6,372,951 B1 | 4/2002 | Ter-Ovanesyan et al. |
| 6,384,296 B1 | 5/2002 | Roe et al. |
| 6,628,978 B1 | 9/2003 | Kondo et al. |
| 7,474,224 B2 | 1/2009 | Long et al. |
| 7,557,719 B1 | 7/2009 | Long |
| 7,661,307 B1 | 2/2010 | Milone |
| 7,916,036 B1 | 3/2011 | Pope et al. |
| 7,924,163 B1 | 4/2011 | Long et al. |
| 7,977,529 B2 | 7/2011 | Bergman et al. |
| 8,085,154 B2 | 12/2011 | Williams et al. |
| 8,375,522 B2 | 2/2013 | York et al. |
| 8,672,842 B2 | 3/2014 | Kenalty et al. |
| 9,253,891 B2 | 2/2016 | Williams |
| 9,283,123 B2 | 3/2016 | Lewis et al. |
| 9,506,886 B1 | 11/2016 | Woodbury et al. |
| 9,810,652 B1 | 11/2017 | Lastinger et al. |
| 9,978,244 B2 | 5/2018 | Ribble et al. |
| 10,022,277 B2 | 7/2018 | Heil et al. |
| 10,115,291 B2 | 10/2018 | Tallent et al. |
| 10,159,607 B2 | 12/2018 | Monson et al. |
| 2002/0067273 A1 | 6/2002 | Jaques et al. |
| 2003/0216670 A1 | 11/2003 | Beggs |
| 2004/0127874 A1 | 7/2004 | Nishizawa et al. |
| 2004/0137959 A1 | 7/2004 | Salzhauer et al. |
| 2004/0220538 A1 | 11/2004 | Panopoulous |
| 2004/0254549 A1 | 12/2004 | Olson et al. |
| 2005/0195085 A1 | 9/2005 | Cretu-Petra |
| 2006/0069360 A1 | 3/2006 | Long et al. |
| 2007/0142799 A1 | 6/2007 | Ales et al. |
| 2007/0270774 A1 | 11/2007 | Bergman et al. |
| 2008/0042835 A1 | 2/2008 | Russell et al. |
| 2008/0091089 A1 | 4/2008 | Guillory et al. |
| 2008/0094226 A1 | 4/2008 | O'Shea et al. |
| 2008/0278336 A1 | 11/2008 | Ortega et al. |
| 2009/0237264 A1 | 9/2009 | Bobey et al. |
| 2009/0243833 A1* | 10/2009 | Huang ................ G06Q 10/087 340/505 |
| 2009/0270770 A1 | 10/2009 | Petrosenko et al. |
| 2010/0004715 A1 | 1/2010 | Fahey |
| 2010/0109879 A1 | 5/2010 | Hamdan |
| 2010/0152688 A1 | 6/2010 | Handwerker et al. |
| 2010/0163315 A1 | 7/2010 | York et al. |
| 2011/0133935 A1* | 6/2011 | Beltmann ............ A61B 5/1113 340/573.1 |
| 2011/0270179 A1 | 11/2011 | Ouyang et al. |
| 2012/0032808 A1 | 2/2012 | Cherubini |
| 2012/0086575 A1 | 4/2012 | Dixon et al. |
| 2012/0150134 A1 | 6/2012 | Wei et al. |
| 2012/0271259 A1 | 10/2012 | Ulert |
| 2012/0277637 A1* | 11/2012 | Vahdatpour ......... A47C 31/123 600/595 |
| 2013/0019405 A1 | 1/2013 | Flanagan et al. |
| 2013/0066289 A1 | 3/2013 | Song et al. |
| 2013/0165809 A1 | 6/2013 | Abir |
| 2013/0296739 A1 | 11/2013 | Schultz |
| 2014/0039351 A1 | 2/2014 | Mix et al. |
| 2014/0121473 A1 | 5/2014 | Banet et al. |
| 2014/0200538 A1 | 7/2014 | Euliano et al. |
| 2014/0221876 A1 | 8/2014 | Eddy |
| 2014/0232556 A1 | 8/2014 | Williams |
| 2014/0266733 A1 | 9/2014 | Hayes et al. |
| 2015/0035671 A1* | 2/2015 | Williams ............ G08B 25/001 340/539.1 |
| 2015/0035677 A1 | 2/2015 | Williams |
| 2015/0039794 A1 | 2/2015 | Williams |
| 2015/0042489 A1 | 2/2015 | LaVon |
| 2015/0045630 A1 | 2/2015 | Poliakine-Baruchi et al. |
| 2015/0109442 A1 | 4/2015 | Derenne et al. |
| 2015/0157512 A1 | 6/2015 | Abir |
| 2015/0170494 A1 | 6/2015 | Hsu et al. |
| 2015/0173667 A1* | 6/2015 | Ben Shalom ........ A61G 5/1043 702/139 |
| 2015/0305620 A1 | 10/2015 | Williams et al. |
| 2016/0008206 A1 | 1/2016 | Devanaboyina |
| 2016/0022218 A1 | 1/2016 | Hayes et al. |
| 2016/0166438 A1 | 6/2016 | Rovaniemi |
| 2017/0020438 A1* | 1/2017 | Wang .................... A61G 7/057 |
| 2017/0035622 A1 | 2/2017 | Wang |
| 2017/0092103 A1* | 3/2017 | Williams ............ A61B 5/6892 |
| 2017/0246063 A1 | 8/2017 | Monson et al. |
| 2018/0116879 A1 | 5/2018 | Williams et al. |
| 2018/0146906 A1 | 5/2018 | Harmeyer |
| 2018/0206794 A1* | 7/2018 | LaBorde ................ G06F 19/00 |
| 2018/0221216 A1* | 8/2018 | Benz .................. A61F 13/53717 |
| 2018/0296401 A1 | 10/2018 | Heil et al. |
| 2018/0311080 A1 | 11/2018 | Potter et al. |
| 2018/0325744 A1 | 11/2018 | Weidman et al. |
| 2018/0354443 A1* | 12/2018 | Ebrahimi ............ B60N 2/2812 |
| 2019/0051137 A1* | 2/2019 | Kilcran ................ A61B 5/0022 |
| 2019/0060137 A1 | 2/2019 | Severns et al. |
| 2019/0209405 A1* | 7/2019 | Sayadi ................ A61B 5/4809 |

FOREIGN PATENT DOCUMENTS

| | | |
|---|---|---|
| GB | 2501561 A | 10/2013 |
| WO | 2014072798 A2 | 5/2014 |
| WO | 2015015282 A1 | 2/2015 |
| WO | 2015015287 A1 | 2/2015 |
| WO | 2015015288 A1 | 2/2015 |
| WO | 2015172246 A1 | 11/2015 |

OTHER PUBLICATIONS

Isquith, A.J., et al., "Surface-Bonded Antimicrobial Activity of an Organosilicon Quaternary Ammonium Chloride," Applied Microbiology, vol. 24, No. 6, Dec. 1972, pp. 859-863.

* cited by examiner

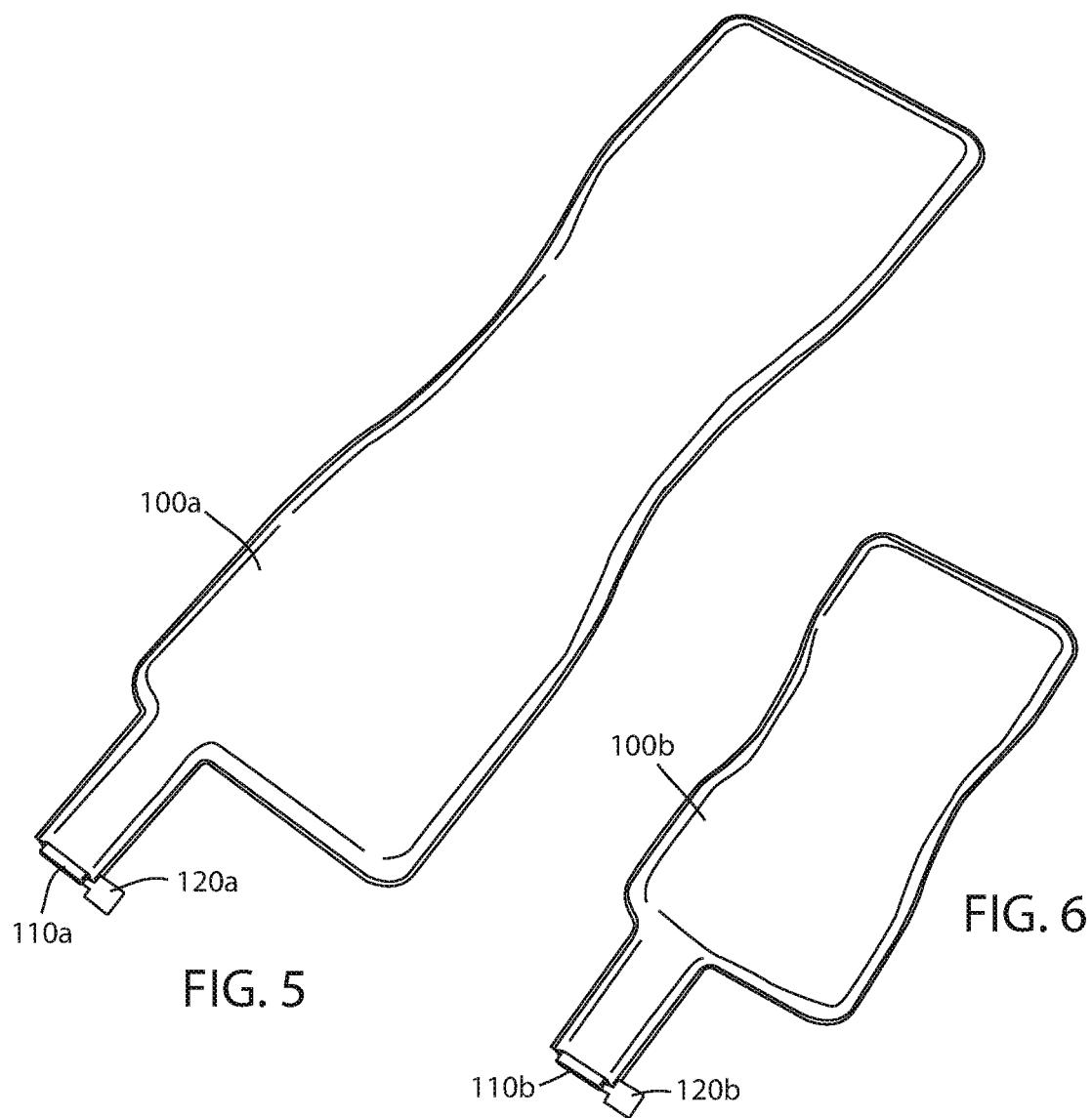
FIG. 5
FIG. 6
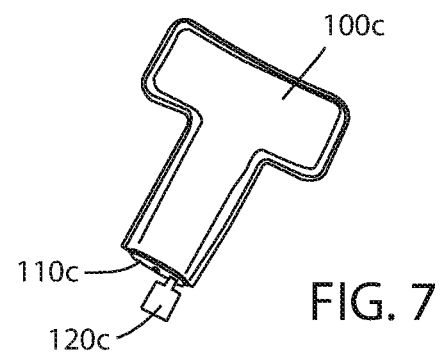
FIG. 7

PATIENT MOVEMENT AND INCONTINENCE NOTIFICATION SYSTEM

CROSS-REFERENCE TO RELATED APPLICATIONS

This application claims priority to and the benefit under 35 U.S.C. § 119(e) of U.S. Provisional Patent Application No. 62/543,436, filed on Aug. 10, 2017, entitled "PATIENT MOVEMENT AND INCONTINENCE NOTIFICATION SYSTEM," by Michael Kilcran et al. and U.S. Provisional Patent Application No. 62/649,088, filed on Mar. 28, 2018, entitled "PATIENT MOVEMENT AND INCONTINENCE NOTIFICATION SYSTEM," by Michael Kilcran et al., the entire disclosures of which are incorporated herein by reference.

BACKGROUND OF THE INVENTION

The present invention generally relates to a patient movement notification system, an incontinence notification system, and a combined patient movement and incontinence notification system and components thereof.

Patient movement notification devices serve to notify a patient's caretaker(s) who may better assist them. Such devices are used for patients who are at a high risk for fall-related injury or for patients who are not healthy enough to stand (post-operative patients, etc.).

Patient movement notification devices are currently in use that include a disposable sensor that is positioned between the patient and a bed, chair, or toilet, and an electronics module that connects to the sensor for generating an alarm when the patient removes pressure from the pad by getting out of bed or up from a chair or toilet. The alarm may be a recorded vocal command, such as "please stay in bed and use the nurse call button if you need assistance" or any other message that the caretaker may wish to record.

Existing patient movement notification devices suffer from several drawbacks. One drawback is that the sensors are considered to be disposable and are typically only to be used for 30 days or less because the sensors are pressure sensitive, and after having pressure continuously applied to the sensor, the sensor may not be able to re-expand when the patient removes pressure. However, hospitals have difficulty monitoring the times of use such that the sensors are often used well beyond the permitted 30-day lifetime. Another drawback is that existing patient movement notification devices include a monitor that either monitors only one sensor pad or monitors several sensor pads of the same type such that when a notification is issued, it is not always clear which sensor pad triggered the notification. Additionally, existing patient movement notification devices often generate alarms too frequently thus becoming a nuisance to the patient and the nurses.

Incontinence notification devices that are known are intended to detect when a patient has urinated or defecated in their bed. Such incontinence devices are placed under the patient's groin area and trigger an alarm upon sensing moisture, often by using conductive traces provided on the upper surface of a moisture-impermeable pad. The moisture-impermeable strips of such incontinence notification devices are disposable and do not serve to absorb urine.

Currently, incontinent notification systems and patient movement notification systems are separate systems each having their own monitor.

SUMMARY

According to one aspect of the present invention, a patient movement notification system is provided, comprising: a first sensor pad comprising a pressure sensor for sensing pressure applied by a patient, and a transmitter circuit for transmitting first wireless signals; a second sensor pad comprising a pressure sensor for sensing pressure applied by a patient, and a transmitter circuit for transmitting second wireless signals; and a monitor having a receiver for receiving the first and second wireless signals, the monitor generating a notification of patient movement in response to one of the first and second wireless signals, wherein the second sensor pad is a different type of sensor pad from said first sensor pad, and wherein the first and second wireless signals include a type code that identifies the type of sensor pad from which the first and second wireless signals are sent.

According to another aspect of the present invention, a notification system for providing patient movement notification and incontinence notification is provided, the notification system comprising: a pressure sensor pad comprising a pressure sensor for sensing pressure applied by a patient and a transmitter for generating a pressure signal in response to the pressure sensor; an incontinence sensor pad comprising an incontinence sensor for sensing moisture due to incontinence, a transmitter associated with the incontinence sensor pad for transmitting a moisture detection signal in response to the incontinence sensor; and a monitor comprising a receiver for receiving the pressure signal and the moisture detection signal, the monitor generates a notification of patient movement in response to the pressure signal, and generates a notification of incontinence in response to receipt of the moisture detection signal.

According to another aspect of the present invention, a patient movement notification system is provided, comprising: a first sensor pad comprising a pressure sensor for sensing pressure applied by a patient, and a transmitter circuit for transmitting first wireless signals; a second sensor pad comprising a pressure sensor for sensing pressure applied by a patient, and a transmitter circuit for transmitting second wireless signals; and a monitor having a receiver for receiving the first and second wireless signals, the monitor generating a notification of patient movement in response to one of the first and second wireless signals, wherein the first and second wireless signals include an active code that identifies whether the sensor pad from which the first and second wireless signals are sent is active.

According to another aspect of the present invention, a patient movement notification system is provided, comprising: a first sensor pad comprising a pressure sensor for sensing pressure applied by a patient, and a transmitter circuit for transmitting first wireless signals; a second sensor pad comprising a pressure sensor for sensing pressure applied by a patient, and a transmitter circuit for transmitting second wireless signals; and a monitor having a receiver for receiving the first and second wireless signals, the monitor generating a notification of patient movement in response to one of the first and second wireless signals, wherein the monitor comprises an input for allowing a user to cause the monitor to terminate responsiveness to all sensor pads from which it receives wireless signals.

According to another aspect of the present invention, a patient movement notification system is provided, comprising: a sensor pad comprising a pressure sensor for sensing pressure applied by a patient, and a transmitter circuit for transmitting a pressure signal; and a monitor having a receiver for receiving the pressure signal from the sensor pad, the monitor generating a notification of patient movement in response to the pressure signal if the pressure signal indicates that the patient is no longer applying pressure to the sensor pad, wherein the monitor comprises a plurality of inputs and a controller coupled to the plurality of inputs, the controller is configured to reset to a factory preset condition in response to simultaneous activation of at least one of the plurality of inputs by the patient caregiver.

According to another aspect of the present invention, a sensor device for a patient activity notification system is provided, the sensor device comprising: a sensor for sensing a patient's activity; a housing including a slot in which two electrical contacts are biased towards one another; a kill tab removably disposed in the slot to connect to an electrical wire extending between the two electrical contacts, the electrical wire permitting current to flow between the two contacts, wherein, when the kill tab is removed from the slot, the electrical wire is pulled from at least one of the two electrical contacts so that current is prevented from flowing through the two electrical contacts; and a controller coupled to the sensor for determining whether to generate a patient activity signal in response to patient activity sensed by the sensor, wherein at least one of the two electrical contacts is coupled to the controller and the controller senses whether current is flowing through the two electrical contacts, and wherein, when the controller senses that current is not flowing through the two electrical contacts, the controller executes a shutdown routine and thereafter no longer executes any further steps or instructions so as to terminate the functionality of the sensor device.

According to another aspect of the present invention, a patient movement notification system is provided, comprising: a sensor pad comprising a pressure sensor for sensing pressure applied by a patient, and a transmitter circuit for transmitting a pressure signal; and a monitor having a receiver for receiving the pressure signal from the sensor pad, the monitor generating a notification of patient movement in response to the pressure signal if the pressure signal indicates that the patient is no longer applying pressure to the sensor pad, wherein the monitor comprises a hold input for allowing a patient caregiver to prevent generation of a notification of patient movement in response to the pressure signal from the sensor pad for a first predetermined time period after the hold input has been activated by the patient caregiver to allow the patient caregiver to temporarily remove the patient from the sensor pad.

According to another aspect of the present invention, an incontinence warning system is provided, comprising: a sensor pad comprising a moisture sensor for sensing moisture due to incontinence; a transmitter associated with the sensor pad for transmitting a moisture detection signal in response to the incontinence sensor; and a monitor having a receiver for receiving the moisture detection signal, the monitor generates a notification of incontinence in response to receipt of the moisture detection signal, wherein the monitor comprises a hold input for allowing a patient caregiver to prevent generation of a notification of incontinence in response to the moisture detection signal from the sensor pad for a first predetermined time period after the hold input has been activated by the patient caregiver to allow the patient caregiver an extended period to respond to an incontinence event.

According to another aspect of the present invention, a patient movement notification system is provided, comprising: a first sensor pad comprising a pressure sensor for sensing pressure applied by a patient, and a transmitter circuit for transmitting first wireless signals; a second sensor pad comprising a pressure sensor for sensing pressure applied by a patient, and a transmitter circuit for transmitting second wireless signals; a monitor comprising a receiver for receiving the first and second wireless signals, the monitor generating a notification of patient movement in response to one of the first and second wireless signals; and a removable key module associated with the monitor and including a module ID code, wherein the first and second sensor pads each include a connector for electrically coupling to the removable key, and wherein the first and second sensor pads receive the module ID code from the removable key and subsequently include the module ID code in the first and second wireless signals.

According to another aspect of the present invention, a patient movement notification system is provided, comprising: a sensor pad comprising a pressure sensor for sensing pressure applied by a patient, and a transmitter circuit for transmitting a pressure signal; and a monitor having a receiver for receiving the pressure signal from the sensor pad, the monitor generating a notification of patient movement in response to the pressure signal if the pressure signal indicates that the patient is no longer applying pressure to the sensor pad, wherein the monitor further includes at least one user input, a speaker, and a controller coupled to the receiver, the user input, and the speaker, wherein the controller is responsive to inputs received from the user input and controls the speaker to play back confirmation tones or pre-recorded vocal confirmations of actuation of the user inputs.

According to another aspect of the present invention, an incontinence sensing system is provided comprising: an incontinence sensor pad comprising first and second electrically conductive tracings on a surface thereof that extend to a terminal portion of the surface; and an incontinence electronic module releasably attached to the terminal portion of the surface of the incontinence sensor pad, the incontinence electronic module comprising: electrical contacts for creating an electrical connection to the first and second electrically conductive tracings, and a circuit coupled to the electrical contacts for sensing moisture across the first and second electrically conductive tracings and for generating an incontinence alarm signal when moisture is sensed.

According to another aspect of the present invention, an incontinence sensing pad is provided comprising: a substrate having a surface; a first electrically conductive tracing on the surface of the substrate, the first electrically conductive tracing includes a first conductive bus connected to a first plurality of interdigitated conductive extensions, the first conductive bus extends to a terminal portion of the surface; and a second electrically conductive tracing on the surface of the substrate, the second electrically conductive tracing includes a second conductive bus connected to a second plurality of interdigitated conductive extensions, the second conductive bus extends to the terminal portion of the surface.

According to another aspect of the present invention, an incontinence chuck is provided comprising: a substrate having a surface; and an absorbent material disposed across at least a portion of the surface of the substrate, wherein the absorbent material includes a color change material that changes color in response to moisture absorbed such that a caretaker can determine a relative volume of moisture that has been absorbed based upon a size of the absorbent material that has changed color.

According to another aspect of the present invention, an incontinence sensing system is provided comprising: an incontinence sensor pad comprising first and second electrically conductive tracings on a surface thereof that extend to a terminal portion of the surface; a temperature sensor for sensing the temperature of a patient lying on the incontinence sensor pad; and an incontinence electronic module attached to the terminal portion of the surface of the incontinence sensor pad, the incontinence electronic module comprising: electrical contacts for creating an electrical connection to the first and second electrically conductive tracings, and a circuit coupled to the electrical contacts for sensing moisture across the first and second electrically conductive tracings and for generating an incontinence alarm signal when moisture is sensed, wherein the circuit generates a bed sore advance warning signal when the temperature sensed by the sensing circuit reaches a threshold temperature.

According to another aspect of the present invention, a patient movement notification system is provided, comprising: a sensor pad comprising a pressure sensor for sensing pressure applied by a patient, and a transmitter circuit for transmitting a pressure signal; a monitor having a monitor transceiver for receiving the pressure signal from the sensor pad, the monitor generating a notification of patient movement in response to the pressure signal if the pressure signal indicates that the patient is no longer applying pressure to the sensor pad; and a nurse call relay device having a nurse call transceiver for providing two-way communication with the monitor transceiver, wherein the monitor transceiver transmits notification signals to the nurse call transceiver, and the nurse call transceiver transmits periodic status signals to the monitor transceiver.

According to another aspect of the present invention, a patient movement notification system is provided, comprising: a toilet seat belt for securing a patient to a toilet, the toilet seat belt comprising: a releasable clip connecting two portions of the seat belt to secure the patient; and a clip sensor for sensing whether the releasable clip is connecting the two portions of the seat belt; and a signal generator for generating an alarm signal when the clip sensor detects that the releasable clip no longer senses that the releasable clip is connecting the two portions of the seat belt.

According to another aspect of the present invention, a patient movement notification system is provided, comprising: a sensor pad comprising a pressure sensor for sensing pressure applied by a patient, and a transmitter circuit for transmitting a pressure signal; a monitor having a monitor transceiver for receiving the pressure signal from the sensor pad, the monitor generating a notification of patient movement in response to the pressure signal if the pressure signal indicates that the patient is no longer applying pressure to the sensor pad; and a motion sensor in communication with the monitor for detecting movement of the patient, wherein the monitor tracks a time period from the last detected movement and generates a notification of non-movement if the motion sensor does not detect movement of the patient for at least a threshold time period.

According to another aspect of the present invention, a patient movement notification system is provided, comprising: a sensor pad comprising a pressure sensor for sensing pressure applied by a patient, and a transmitter circuit for transmitting a pressure signal; a monitor having a monitor transceiver for receiving the pressure signal from the sensor pad, the monitor generating a notification of patient movement in response to the pressure signal if the pressure signal indicates that the patient is no longer applying pressure to the sensor pad, wherein the notification of patient movement is transmitted to a mobile communication device of a caregiver.

According to another aspect of the present invention, an incontinence warning system is provided, comprising: a sensor pad comprising a moisture sensor for sensing moisture due to incontinence; a transmitter associated with the sensor pad for transmitting a moisture detection signal in response to the incontinence sensor; and a monitor having a receiver for receiving the moisture detection signal, the monitor generates a notification of incontinence in response to receipt of the moisture detection signal, wherein the notification of incontinence is transmitted to a mobile communication device of a caregiver.

According to another aspect of the present invention, a patient movement notification system is provided, comprising: a sensor pad comprising a pressure sensor for sensing pressure applied by a patient, and a transmitter circuit for transmitting a pressure signal; and a monitor having a receiver for receiving the pressure signal from the sensor pad, and a controller coupled to the receiver, the controller determines whether the pressure signal indicates that the patient is no longer applying pressure to the sensor pad and generates a notification of patient movement in response to the pressure signal if the pressure signal indicates that the patient is no longer applying pressure to the sensor pad; and at least one light for illuminating an area near the patient, wherein the controller controls the at least one light to selectively illuminate the area near the patient.

According to another aspect of the present invention, a patient movement notification system is provided, comprising: a sensor pad comprising a pressure sensor for sensing pressure applied by a patient, and a transmitter circuit for transmitting a pressure signal; a light strip for selectively illuminating an area where the patient is located; and a monitor having a receiver for receiving the pressure signal from the sensor pad, the monitor generating a notification of patient movement in response to the pressure signal if the pressure signal indicates that the patient is no longer applying pressure to the sensor pad, wherein the monitor is communicatively coupled to the light strip for controlling the light strip to illuminate the area in response to the pressure signal if the pressure signal indicates that the patient is no longer applying pressure to the sensor pad.

According to another aspect of the present invention, a patient movement notification system is provided comprising: a sensor pad comprising a pressure sensor for sensing pressure applied by a patient, and a transmitter circuit for transmitting a pressure signal; and a monitor having a receiver for receiving the pressure signal from the sensor pad, the monitor generating a notification of patient movement in response to the pressure signal if the pressure signal indicates that the patient is no longer applying pressure to the sensor pad, wherein the monitor further includes a touchscreen display and a controller coupled to the receiver and the touchscreen display, wherein the controller is responsive to inputs received from the touchscreen display and controls images displayed on the touchscreen display.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 5 is a perspective view of a bed pressure sensor pad of the notification system shown in FIG. 2;

FIG. 6 is a perspective view of a chair pressure sensor pad of the notification system shown in FIG. 2;

FIG. 7 is a perspective view of a toilet pressure sensor pad of the notification system shown in FIG. 2;

DETAILED DESCRIPTION OF PREFERRED EMBODIMENTS

Figure 1:
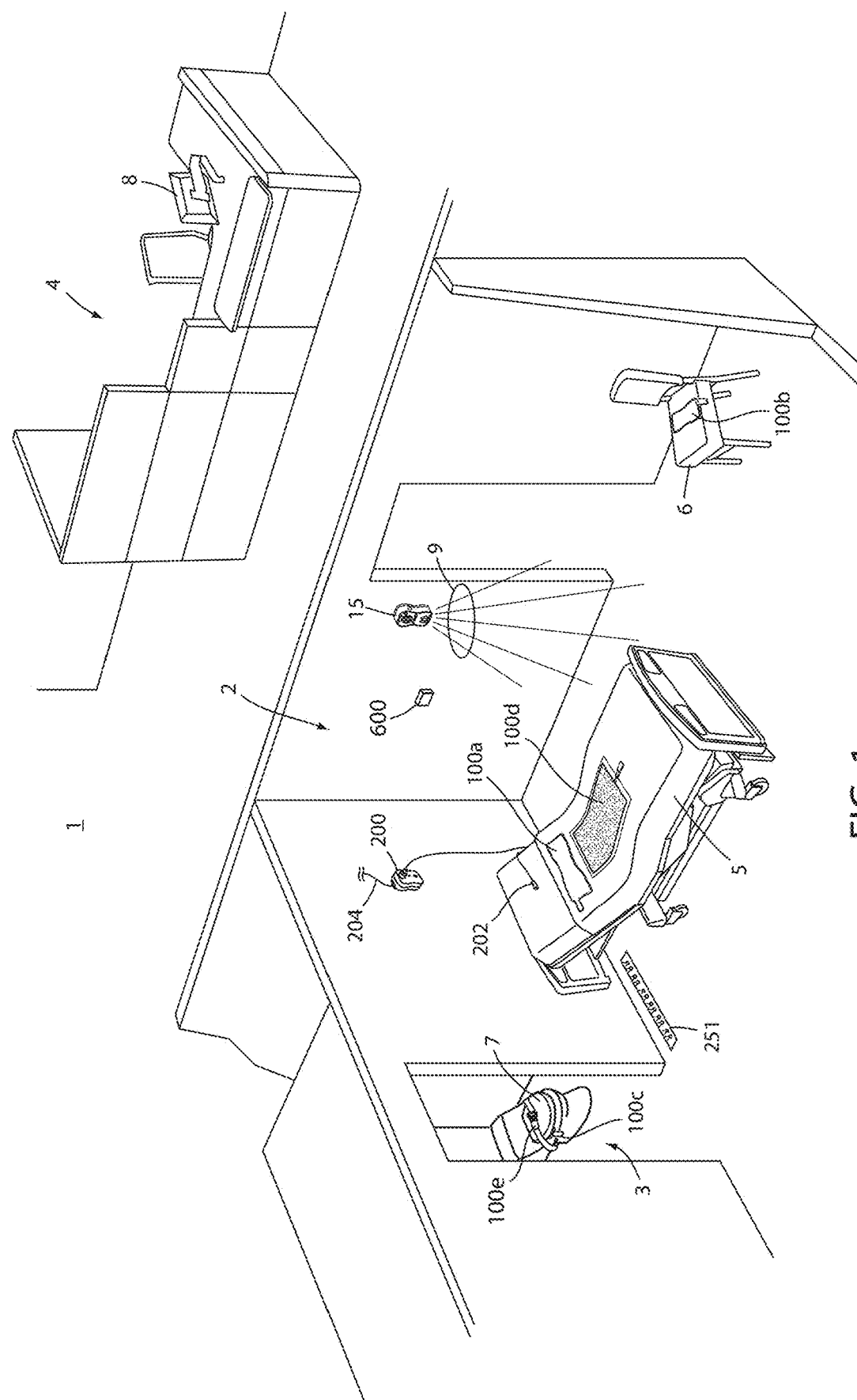
FIG. 1 is a perspective view of a portion of a healthcare facility in which the notification system described herein may be implemented.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

Various embodiments of a notification system are described herein. In some embodiments, the notification system issues a notification upon detection of patient movement. In other embodiments, the notification system issues a notification upon detection of patient incontinence. In still other embodiments, the notification system issues notifications upon detection of either or both patient movement and patient incontinence. In each embodiment, the notification system includes at least one sensor pad and a monitor. The configurations of the sensor pad and the monitor may vary from embodiment to embodiment.

FIG. 1 depicts an example of a portion of a care center 1 having at least one patient room 2 with a bathroom 3. FIG. 1 also shows, along with FIG. 2, an example of a notification system that may be used in the care center 1. The care center 1 may further include a nursing station 4 having a nurse call/monitoring system 8. As used herein, a care center 1 may be a hospital or other medical facility, or may be an assisted living center, nursing home, or hospice, etc. It should be appreciated, however, that the embodiments described herein are not limited to use in such a facility, but may also be used at a residence where a resident needs to be monitored to prevent falling or where a caretaker needs to be aware of an incontinence event by the resident.

As shown, the patient room may include a bed 5 and a chair 6, which may be a wheelchair. The bathroom 3 may include a toilet 7. As apparent from FIG. 1, a patient in room 2 may be at rest either in the bed 5 or in the chair 6 or may be seated on the toilet 7. When the patient is in any one of these locations and attempts to get up and move from one of these locations without needed assistance, there is a risk of injury from a fall. Thus, a notification system 10 is provided to sense when the patient is attempting to move from one of these locations and to warn the patient not to attempt to move. The notification system 10 may further notify a nurse that the patient is attempting to move.

To monitor events such as attempted movement and/or incontinence of the patient, at least one sensor pad (100*a*, 100*b*, 100*c*, 100*d*) is provided that communicates with a monitor 15 that may be mounted within the patient room 2 either on the wall, the chair, the bed, or outside the patient's room. The at least one sensor pad (100*a*, 100*b*, 100*c*, 100*d*) may include a bed pressure sensor pad 100*a*, a chair pressure sensor pad 100*b*, a toilet pressure sensor pad 100*c* (and/or a toilet seatbelt 100*e* (FIG. 2)), and/or an incontinence sensor pad 100d. The incontinence sensor pad 100d may be placed on the bed 5 or chair 6. As explained further below, the monitor 15 may be configured to only communicate with one sensor pad of each type. In other words, the monitor 15 may be configured to only communicate with one bed pressure sensor pad 100a, one chair pressure sensor pad 100b, one toilet pressure sensor pad 100c, one incontinence sensor pad 100d, and one toilet seat belt 100e. Similarly, the nurse call relay device 200 may be configured to only communicate with one monitor 15. For example, a patient movement notification system 10 may include: a first sensor pad (e.g., 100a) comprising a pressure sensor 125 (FIG. 9) for sensing pressure applied by a patient, and a transmitter circuit 127 for transmitting first wireless signals; a second sensor pad (e.g., 100b) comprising a pressure sensor 125 for sensing pressure applied by a patient, and a transmitter circuit 127 for transmitting second wireless signals; and a monitor 15 having a receiver (or transceiver 80, FIG. 4) for receiving the first and second wireless signals, the monitor 15 generating a notification of patient movement in response to one of the first and second wireless signals. The second sensor pad (e.g., 100b) is a different type of pad from the first sensor pad (e.g., 100a), and the first and second wireless signals include a type code that identifies the type of sensor pad from which the first and second wireless signals are sent.

The first and second wireless signals may include an active code that identifies whether the sensor pad from which the first and second wireless signals are sent is active. By "active," it is meant that the patient is currently applying pressure to the sensor pad. By knowing which pressure sensor pad is active (if any), the monitor 15 may trigger a notification if pressure is not sensed by the active pressure sensor pad for a predetermined time period as discussed further below.

In the context of a combined movement and incontinence notification system, an example of a notification system 10 for providing patient movement notification and incontinence notification includes: a pressure sensor pad (e.g., one of 100a, 100b, 100c) comprising a pressure sensor 125 (FIG. 9) for sensing pressure applied by a patient and a transmitter 127 for generating a pressure signal in response to the pressure sensor 125; an incontinence sensor 100d for sensing moisture due to incontinence, the incontinence sensor 100d comprising a moisture sensor 145 (FIG. 10) and a transmitter 147 for transmitting a moisture detection signal in response to the moisture sensor 145; and a monitor 15 comprising a receiver (or transceiver 80, FIG. 4) for receiving the pressure signal and the moisture detection signal, the monitor 15 generates a notification of patient movement in response to the pressure signal, and generates a notification of incontinence in response to receipt of the moisture detection signal. The pressure signal and the moisture detection signal include a type code that identifies the type of sensor from which the signals are sent. By knowing whether a signal is coming from a pressure sensor pad or an incontinence sensor pad, monitor 15 can respond differently to such a signal. Examples of the different responses are discussed further below.

As shown in FIG. 1, a nurse call relay device 200 may also be provided that receives wireless signals from the monitor 15 and may respond to such wireless signals by transmitting a signal to the nurse call/monitoring system 8 at the nursing station 4 using the existing nurse call wiring system 204. As described below, the nurse call relay device 200 may have a plug for plugging into an existing wall port of the existing nurse call wiring system 204 and may have a receptacle for receiving the plug of the existing nurse call button 202. In this manner, nurse call relay device 200 may be able to use the existing nurse call wiring system 204 without disruption to the existing nurse call button 202 functionality. Additional details of the nurse call relay device 200 are discussed below with reference to FIGS. 11, 14, and 15.

The notification system 10 may also include one or more lighting strips 251 that may be disposed to illuminate a path from the bed 5 to the bathroom 3. The monitor 15 may be configured to send a signal to such a lighting strip 251 to cause the strip to illuminate this path. For example, when it is detected via bed pressure sensor pad 100a that the patient has attempted to get out of bed, the monitor may cause lighting strip 251 to illuminate so that the patient can better see the path to the bathroom. It should be noted that the monitor 15 may be configured to illuminate other lights within the room 2 or the bathroom 3 using existing wireless lighting control technology. Further, as discussed below, the monitor 15 may include one or more illumination lights 84 for projecting light 9 (FIGS. 1, 2, and 4) from the monitor 15 towards the floor of the room 2.

Figure 3:
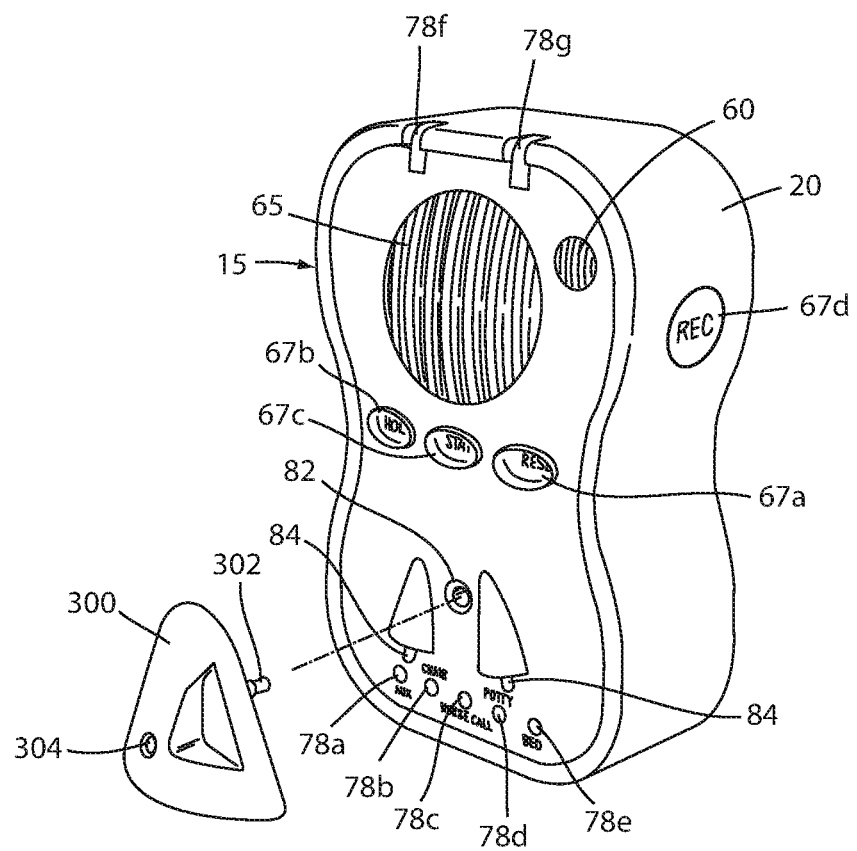
FIG. 3 is a perspective view of a monitor of the notification system shown in FIG. 2.
Figure 4:
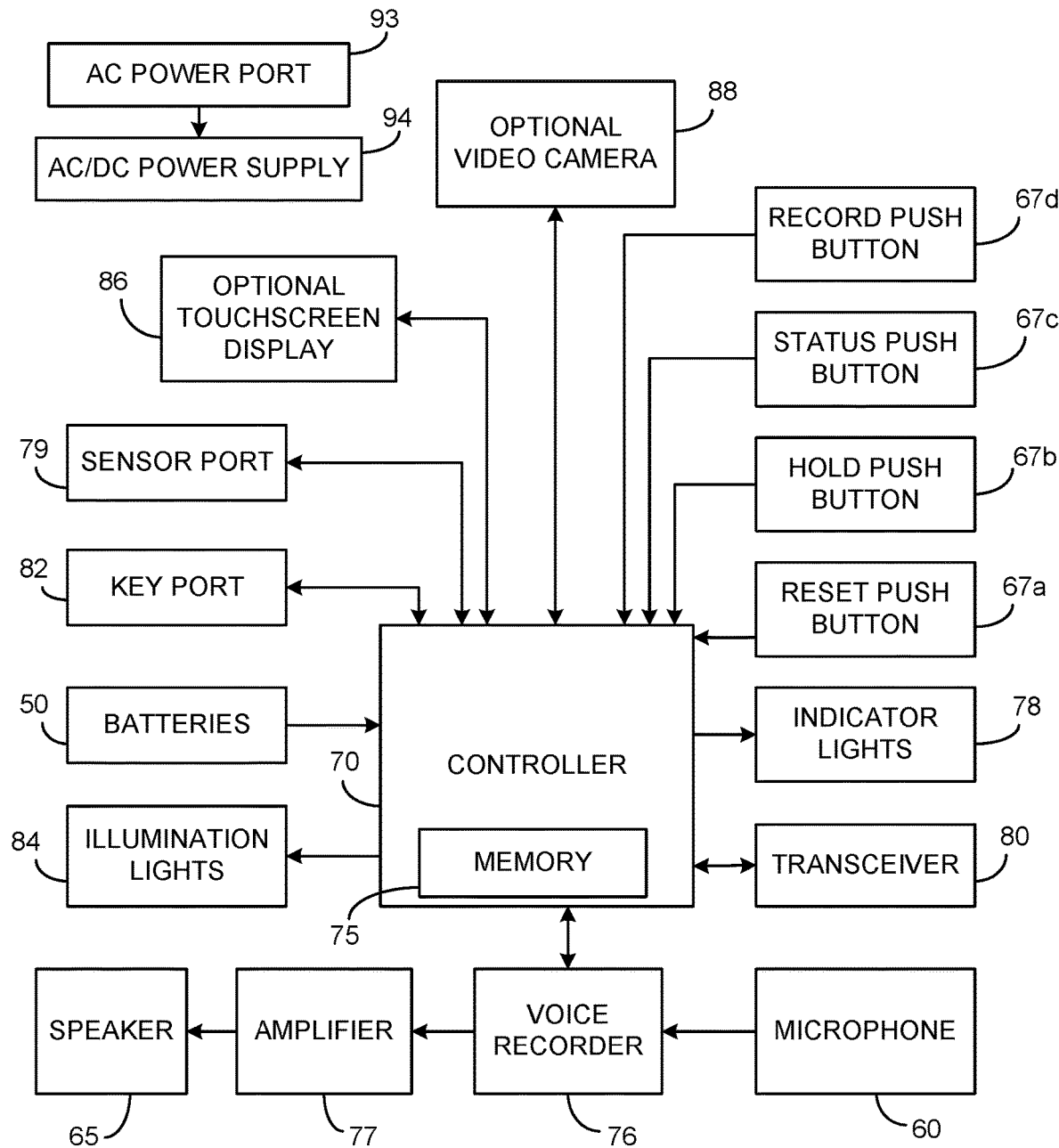
FIG. 4 is a block diagram of an electrical circuit of the monitor shown in FIG. 3.
Figure 21:
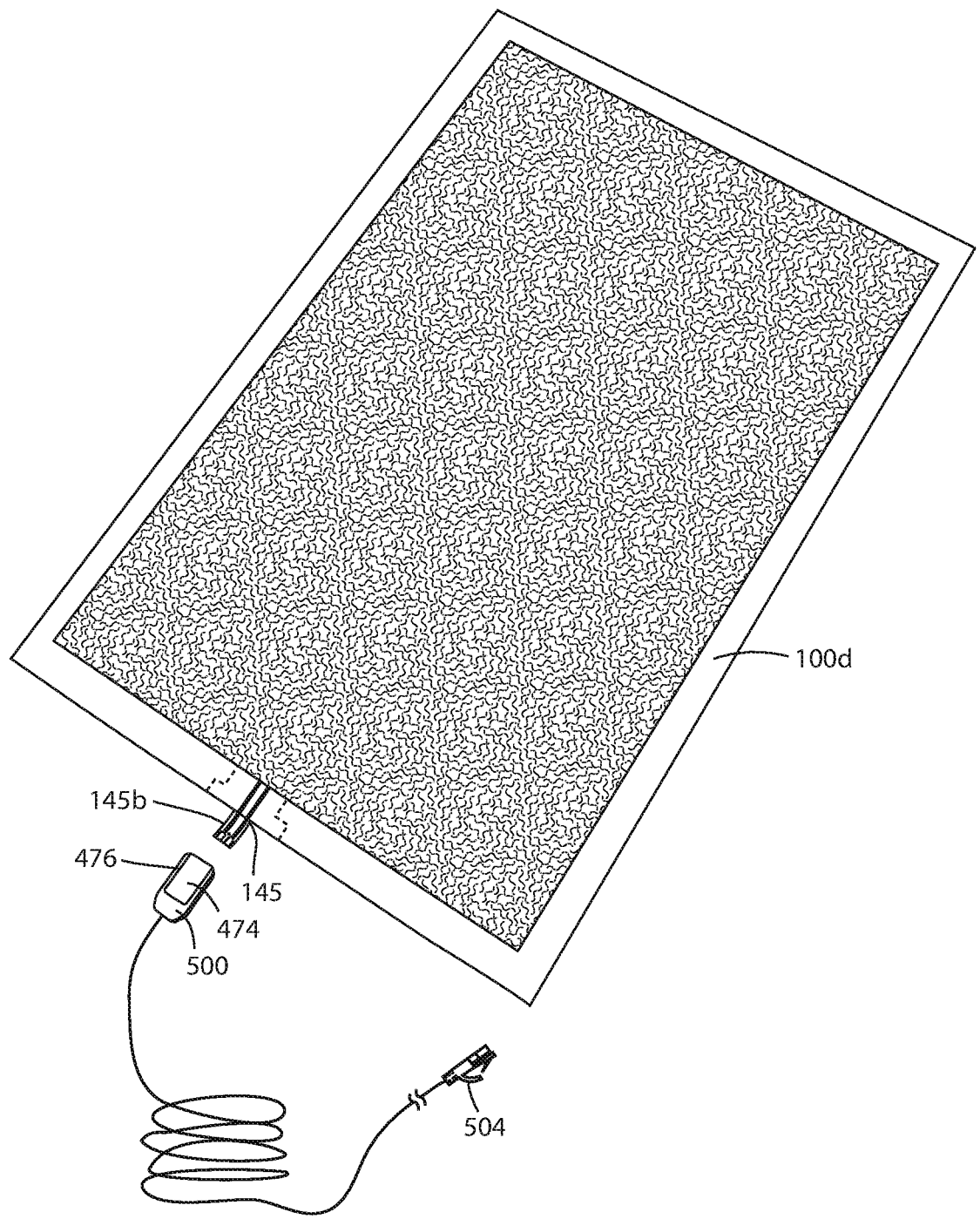
FIG. 21 is a perspective view of the incontinence sensor pad shown in FIG. 18 and a wired module that connects to the terminal end of the incontinence sensor pad.
Figure 22:
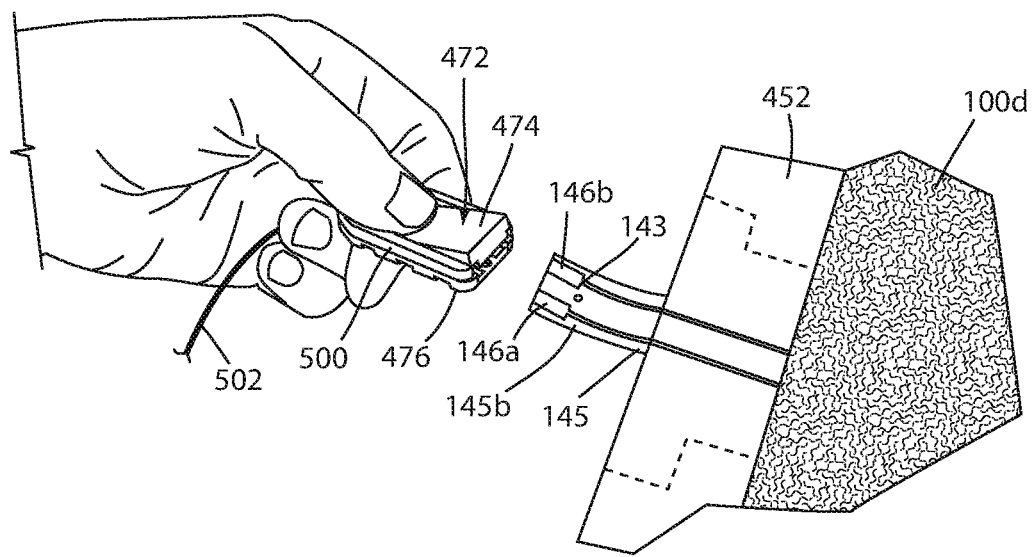
FIG. 22 is a close-up perspective view showing the terminal end of the incontinence sensor pad and the wired module shown in FIG. 21.
Figure 23:
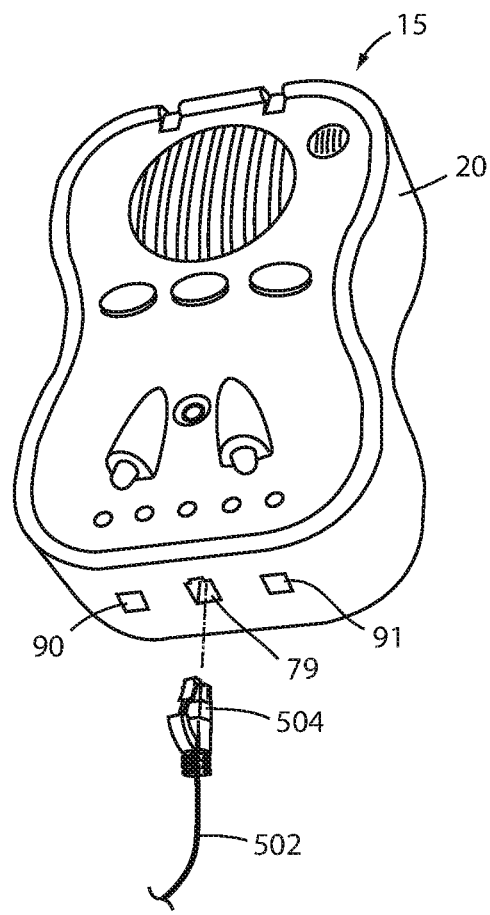
FIG. 23 is a perspective view showing the front and bottom of the monitor shown in FIG. 3 with the plug from the wired module shown in FIGS. 21 and 22.
Figure 24:
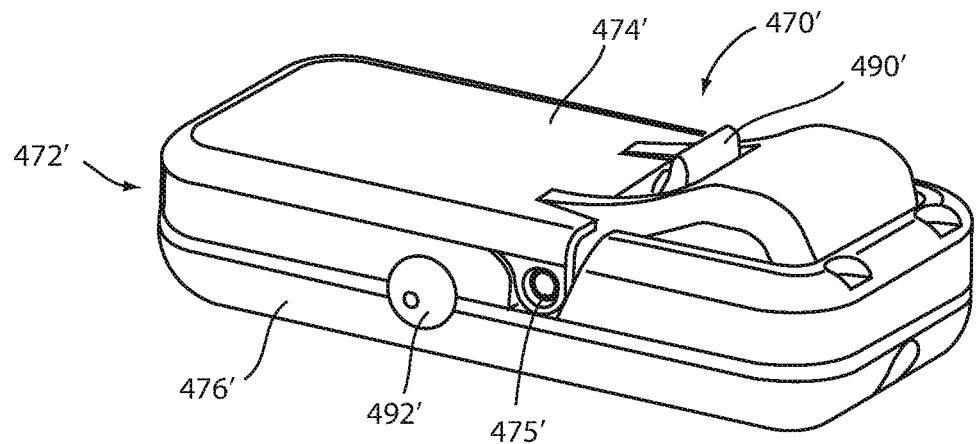
FIG. 24 is a perspective view of a quick connect wireless module in the closed position that connects to the terminal end of the incontinence sensor pad shown in FIG. 18A or 18B.
Figure 25:
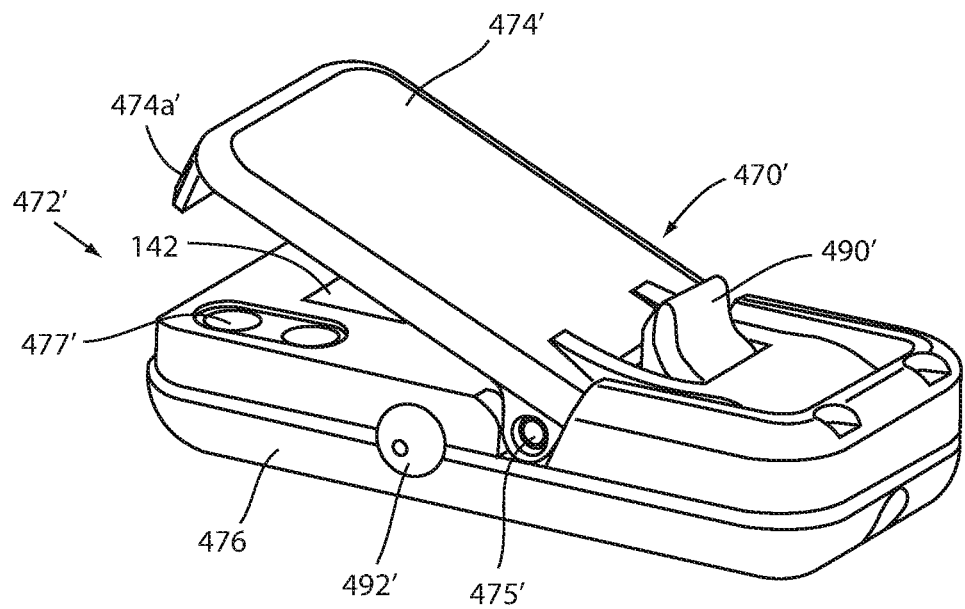
FIG. 25 is a perspective view of quick connect wireless module of FIG. 24 shown in the open position.
Figure 26:
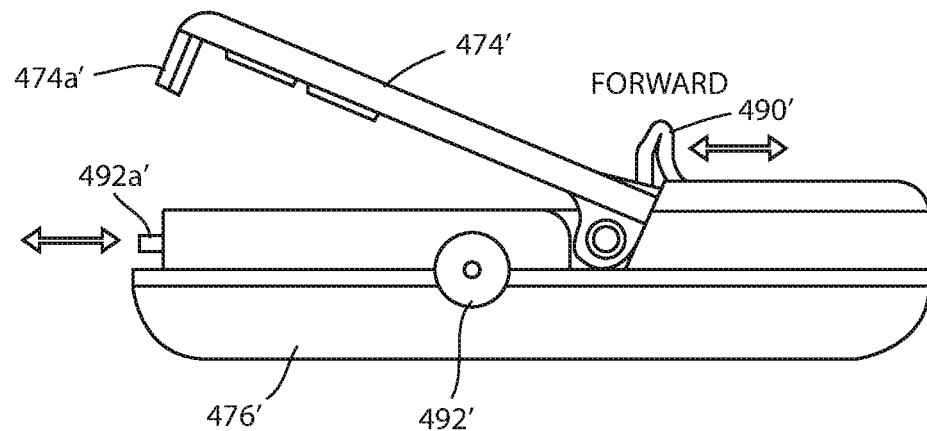
FIG. 26 is a side view of the wireless module shown in FIG. 24 in the open position with the locking pin extended.
Figure 27:
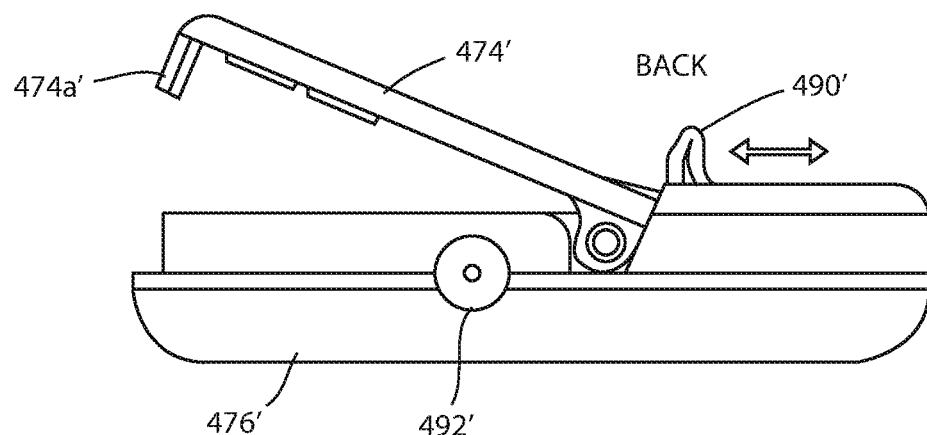
FIG. 27 is a side view of the wireless module shown in FIG. 24 in the open position with the locking pin retracted.

The monitor 15 may be configured as shown in FIG. 3 to include a housing 20 that contains the electronics (described below) and at least one battery 50 (FIG. 4). The electronics that may be included in housing 20 are shown in FIG. 4. As shown, the monitor 15 includes a sensor port 79 that may be a connector receptacle to receive a plug end of a wire extending from a sensor pad, such as incontinent sensor pad 100d as shown in FIGS. 21-23. The electronics may take any form of circuitry capable of storing a voice recording, playing the voice recording back when determining that the patient is moving in response to a signal from the active sensor pad. As such, the electronics may include any one or more of a microphone 60, a speaker 65, a RESET push button 67a, a HOLD push button 67b, a STATUS push button 67c, a RECORD push button 67d, a controller 70 (which may be a microprocessor, digital signal processor, or discrete electronic components), memory 75 (which may be memory internal to a microprocessor), a voice recorder 76, an audio amplifier 77, a sensor port 79 for connecting to a sensor pad, one or more batteries 50, a transceiver 80, indicator lights 78, a key port 82, illuminator lights 84, an optional nurse call port 90 (FIGS. 17 and 23), and a data port 91 (FIGS. 17 and 23), which may be a USB or micro-USB port or plug, for example.

Transceiver 80 may be configured to transmit information (which may include alarms and other data) to the nurse call/monitoring system 8 via the nurse call relay device 200 or directly (if so equipped). Transceiver 80 may also be configured to transmit information to a mobile communication device 250 (FIG. 2) either directly or through a router or the nurse call/monitoring system 8. As used herein "mobile communication device" may include a smart phone, smart watch, a pager, a cell phone, etc. This information may then be stored in an automated records database of the healthcare facility or otherwise stored at the nursing station 4, and/or stored in a cloud storage server or the monitor 15. The information may include any one or more of the following: warnings that a patient has had an incontinence event; warnings of a patient getting out of bed, out of a chair or wheelchair, or off of a toilet; the time and date of issuance of the warnings and the time and date the patient returned to bed or the chair; the time it took for staff to respond to an incident warning; the action taken; the pad type (i.e., bed, chair, toilet, incontinence) to which the warning relates; the room number; warnings of a lost pad; and warnings of approaching end of life of the sensor pads with a time and date stamp. The time and date stamps may be generated at the receiving side of the information and stored in the records database. The records database may be a database such as a Cerner® or EPIC® records database. By storing information relating to such incidents, the system may be auditable. Other data that may be recorded includes: expiration warning and actual expiration of any pad type, complete loss of power or monitor shutdown, and low battery threshold of all components (including the monitor, pads, nurse call relay device, and all other peripheral devices).

Transceiver 80 may thus be in communication with a nursing station alarm switchboard so as to generate appropriate alarm signals at the nursing station 4 that identifies the patient or room and the warnings so that the staff can take appropriate action.

Controller 70 may also store historical information in memory 75 (or otherwise transmit the necessary information to the nursing station 4 and/or records database so that the historical information may be stored). Such historical information may include times of day that the patient historically suffers from incontinence and/or gets out of bed or attempts to get out of bed. By tracking this historical information, nurses may be sent a warning via cell phone text or other alarm mechanism to their mobile communication device 250 to check on the patient just prior to those historical times so as to avoid the incontinence event altogether.

In some facilities, video monitoring may be used to identify when a patient has or is about to get out of bed. While this technique can be effective, there are often too many monitors for one person to watch. By using the notification system 10 in conjunction with the video monitoring system, a nurse or other person watching the video monitors may be warned to view a particular patient, when, for example, the fall prevention alarm is triggered. If the patient has or is attempting to get out of bed, a nurse may be sent to that room. However, if the patient has merely moved in bed so as to trigger the fall prevention alarm, the person watching the video monitors may see that a nurse does not need to respond in person and simply reset the alarm remotely. This cuts down on false notifications that would otherwise consume significant time of the nursing staff.

As shown in FIG. 3, the monitor 15 may include a plurality of indicator lights 78a-78g. The first indicator light 78a indicates the status of a connection with an auxiliary (AUX) device, which may be the incontinence sensor pad 100d, toilet seatbelt 100e, or any other peripheral device. The second indicator light 78b indicates the status of a connection with the chair pressure sensor pad 100b. The third indicator light 78c indicates the status of a connection with the nurse call relay device 200. The fourth indicator light 78d indicates the status of a connection with the toilet pressure sensor pad 100c. The fifth indicator light 78e indicates the status of a connection with the bed pressure sensor pad 100a. Indictor lights 78f and 78g may be used to show when the monitor 15 is powered on, when it is recording, when there is a notification/alarm event, which pad is active, and/or when a hold has been placed on an alarm. Lights 78f and 78g may also be used to show when data is being transferred.

The monitor 15 may optionally include a touch screen display 86 (FIG. 4), which may supplement or take the place of the various push buttons and indicator lights. The display 86 may also be used to enable a dedicated face-to-face video conference between the patient and a caretaker. The controller 70 is coupled to the touch screen display 86 to receive inputs therefrom and to alter the information displayed thereon.

Figure 2:
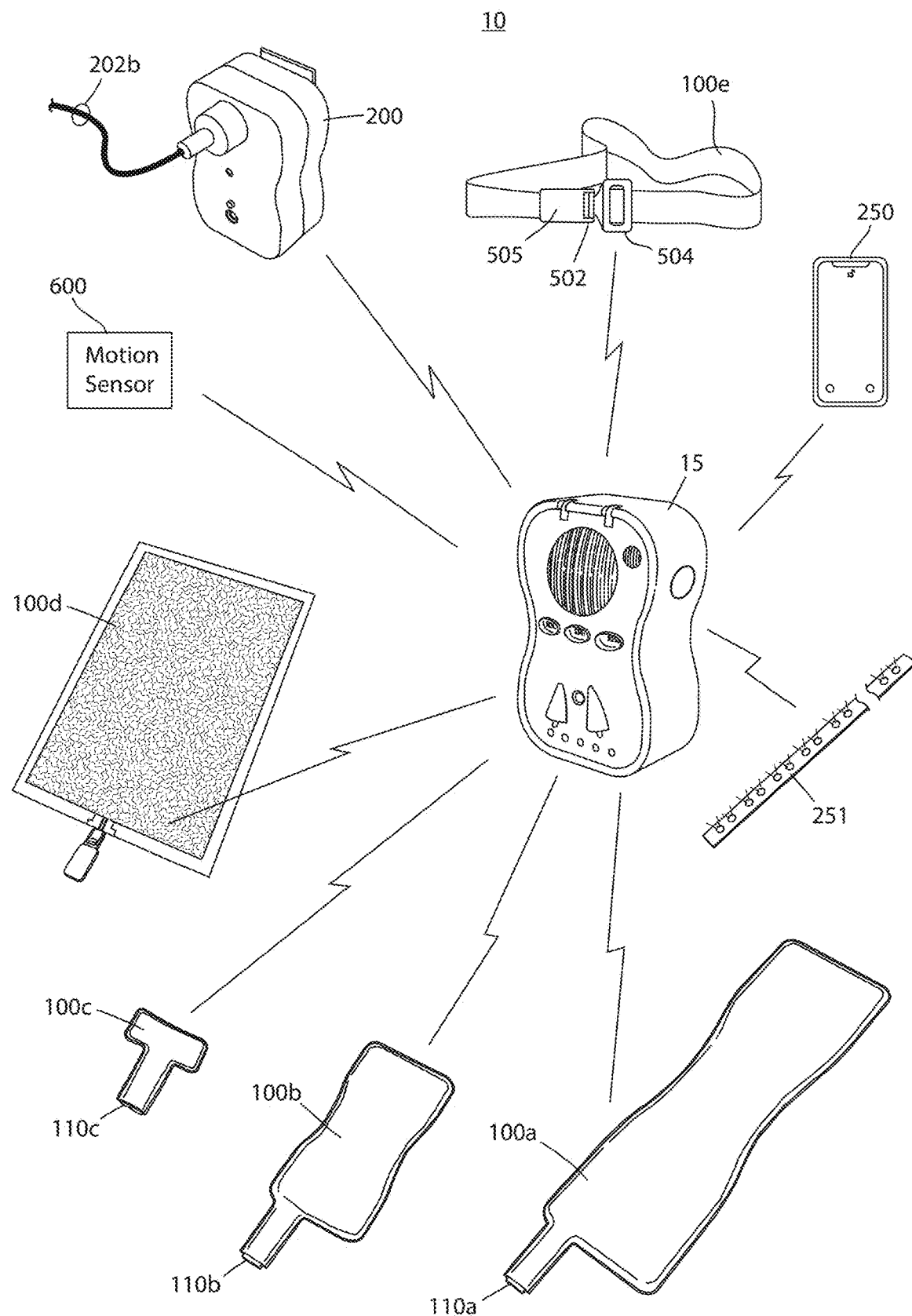
FIG. 2 is a perspective view of the components of the notification system described herein.

In addition, the monitor 15 may include an integrated video camera 88 that permits video monitoring by a caretaker. The system 10 may be configured such that video from camera 88 is only streamed to a caretaker when a notification event has taken place or when requested by the caretaker. By also turning on one or more lights upon detecting an event, the camera 88 will be better able to capture video during nighttime. The video from camera 88 may be streamed to any type of mobile communication device 250 (FIG. 2).

The monitor 15 may further include an optional nurse call port 90 (FIGS. 17 and 23), which allows a simple hopper cord to be plugged into the monitor 15 and plugged in at the other end to the nurse call wiring system 204 so that the monitor 15 may communicate directly with the nurse call/monitoring system 8 without requiring a nurse call relay device 200.

The monitor 15 may further include a data port 91 (FIGS. 17 and 23) that may be on the bottom or back of the monitor 15. The data port 91 facilitates direct connection to the electronics modules 110 of the sensor pads 100a-100c and the electronics module 130 of the incontinence pad 100d. The data port may also be used for updates and diagnostics or other functions.

Figure 17:
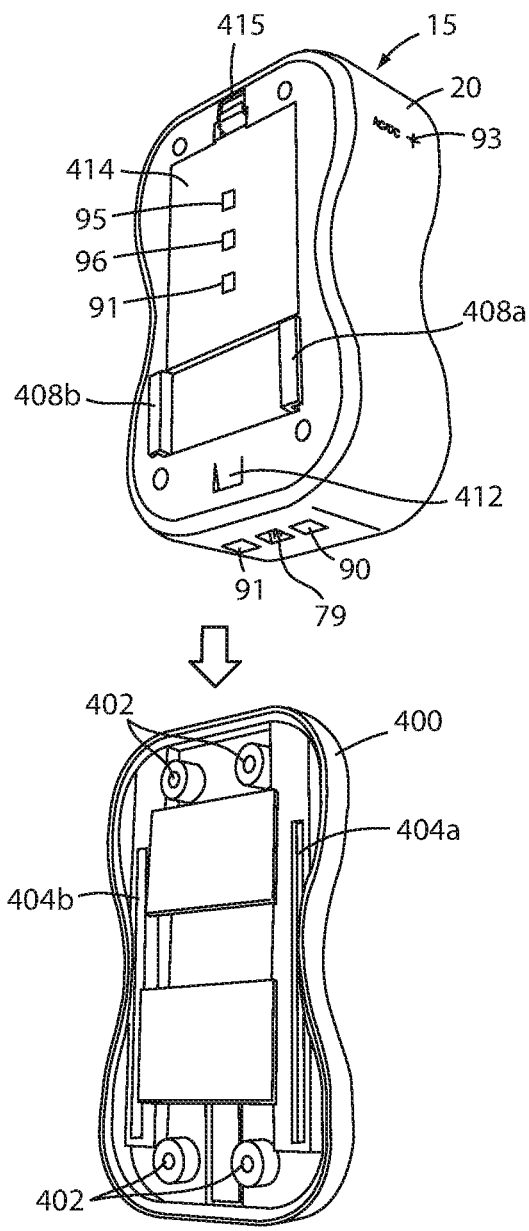
FIG. 17 is a perspective view of the rear of the monitor and mounting plate shown in FIG. 16.

As shown in FIG. 17, the monitor 15 may also optionally include a switch 95 for allowing the operating mode to be set, and a switch 96 to allow the user to adjust the tone of the alarms.

As shown in FIGS. 4 and 17, the monitor 15 may also include an AC power port 93 and an AC/DC converter power supply 94 so that the monitor 15 may run off of AC power.

It should further be noted that movement notification signals or incontinent event notifications signals can be sent to the patient caretaker's (or attending nurse's) mobile communication device 250. Such notification signals could be sent directly from monitor 15, directly from the incontinence sensor pad, in-bed sensor, diaper, or underwear, or from any of the aforementioned devices via nurse call relay device 200, nurse call/monitoring system 8, or a router. Specifically, notification signals may be sent:

1. direct from sensor pad 100a-100d to monitor 15;
2. direct from sensor pad 100a-100d to nurse call relay device 200 to nurse call/monitoring system 8;
3. direct from sensor pad 100a-100d to nurse call/monitoring system 8;
4. direct from sensor pad 100a-100d to mobile communication device 250;
5. direct from sensor pad 100a-100d to a home hub (i.e., Amazon Echo®, Apple HomePod®, or Google Home®);
6. from sensor pad 100a-100d to monitor 15 to nurse call relay device 200 to nurse call/monitoring system 8;
7. from sensor pad 100a-100d to monitor 15 to nurse call/monitoring system 8;
8. from sensor pad 100a-100d to monitor 15 to mobile communication device 250;
9. from sensor pad 100a-100d to monitor 15 to a home hub;
10. from sensor pad 100a-100d to monitor 15 to nurse call relay device 200 to nurse call/monitoring system 8 to mobile device 250;
11. from sensor pad 100a-100d to monitor 15 to nurse call/monitoring system 8 to mobile device 250;
12. from sensor pad 100a-100d to monitor 15 to nurse call relay device 200 to nurse call/monitoring system 8 to a home hub;
13. from sensor pad 100a-100d to monitor 15 to nurse call/monitoring system 8 to a home hub;

14. from sensor pad 100*a*-100*d* to a router to nurse call relay device 200 to nurse call/monitoring system 8;
15. from sensor pad 100*a*-100*d* to a router to nurse call/monitoring system 8;
16. from sensor pad 100*a*-100*d* to a router to nurse call relay device 200 to nurse call/monitoring system 8 to mobile device 250;
17. from sensor pad 100*a*-100*d* to a router to nurse call/monitoring system 8 to mobile device 250;
18. from sensor pad 100*a*-100*d* to a router to nurse call relay device 200 to nurse call/monitoring system 8 to a home hub;
19. from sensor pad 100*a*-100*d* to a router to nurse call/monitoring system 8 to a home hub;
20. from sensor pad 100*a*-100*d* to a router to mobile device 250;
21. from sensor pad 100*a*-100*d* to a router to a home hub; and/or
22. direct from sensor pad 100*a*-100*d* to an electronics module integrated into bed 5.

The notification signals may be transmitted using any wireless RF technology or protocol, such as Wi-Fi, cellular, Bluetooth®, LoRa®, or any other wireless protocol, for example.

Having generally described the structure of the monitor 15, the structures of the pressure sensor pads (100*a*, 100*b*, 100*c*), the incontinence sensor pad 110*d*, and the nurse call relay device 200 will now be described.

Figure 8A:
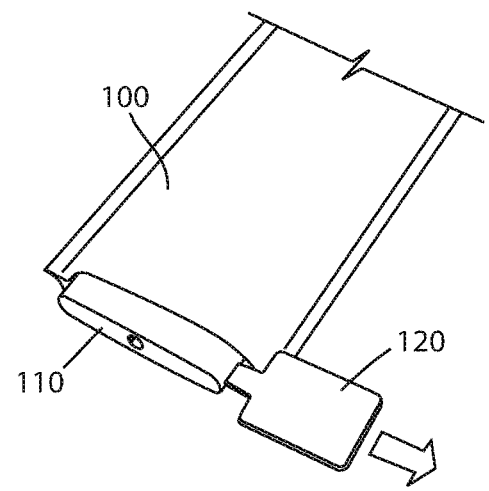
FIG. 8A is a close-up of the end of any one of the bed, chair, or toilet pressure sensor pads shown in FIGS. 5-7.
Figure 8B:
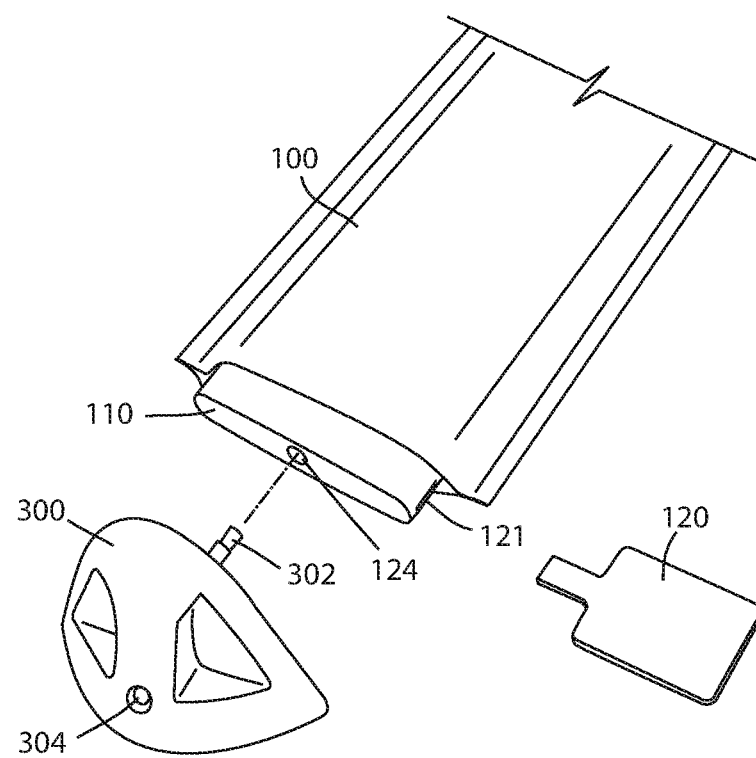
FIG. 8B is another close-up of the end of any one of the bed, chair, or toilet pressure sensor pads shown in FIGS. 5-7 with an electronic key.

FIG. 5 shows the bed pressure sensor pad 100*a*, which includes a pressure sensor pad electronic circuit 110*a* to which a kill tab 120*a* is attached through a slot 121 (FIG. 8B). FIG. 6 shows the chair pressure sensor pad 100*b*, which includes a pressure sensor pad 110*b* to which a kill tab 120*b* is attached. FIG. 7 shows the toilet pressure sensor pad 100*c*, which includes a pressure sensor pad electronic circuit 110*c* to which a kill tab 120*c* is attached. FIGS. 8A and 8B show a close-up of an end of a pressure sensor pad (generically referred to as 100), which may be any one of sensor pads 100*a*, 100*b*, and 100*c*. Pressure sensor pad 100 includes a pressure sensor pad electronic circuit (generically referred to as 110), which may be any one of the pressure sensor pad electronic circuits 110*a*, 110*b*, and 110*c* and a kill tab (generically referred to as 120), which may be any one of kill tabs 120*a*, 120*b*, and 120*c*. The kill tabs 120 are provided to cause the electronic circuits to disable themselves to prevent further use of the sensor pads 100. As described in more detail below, pulling of a kill tab 120 may cause the associated electronic circuit 110, 130 to signal the monitor 15 that it has been disabled, which responds by eliminating the pairing with sensor pad 100 so that it does not subsequently query whether communication with the sensor pad 100 is lost.

The kill tab 120 is removably disposed in the slot 121 to connect to an electrical wire extending between two electrical contacts. The electrical wire permits current to flow between the two contacts. When the kill tab 120 is removed from the slot 121, the electrical wire is pulled from at least one of the two electrical contacts so that current is prevented from flowing through the two electrical contacts. At least one of the two electrical contacts is coupled to a controller (115, 135, 155, FIGS. 9-11) and the controller senses whether current is flowing through the two electrical contacts. When the controller senses that current is not flowing through the two electrical contacts, the controller executes a shutdown routine and thereafter no longer executes any further steps or instructions so as to terminate the functionality of the sensor device.

Figure 9:
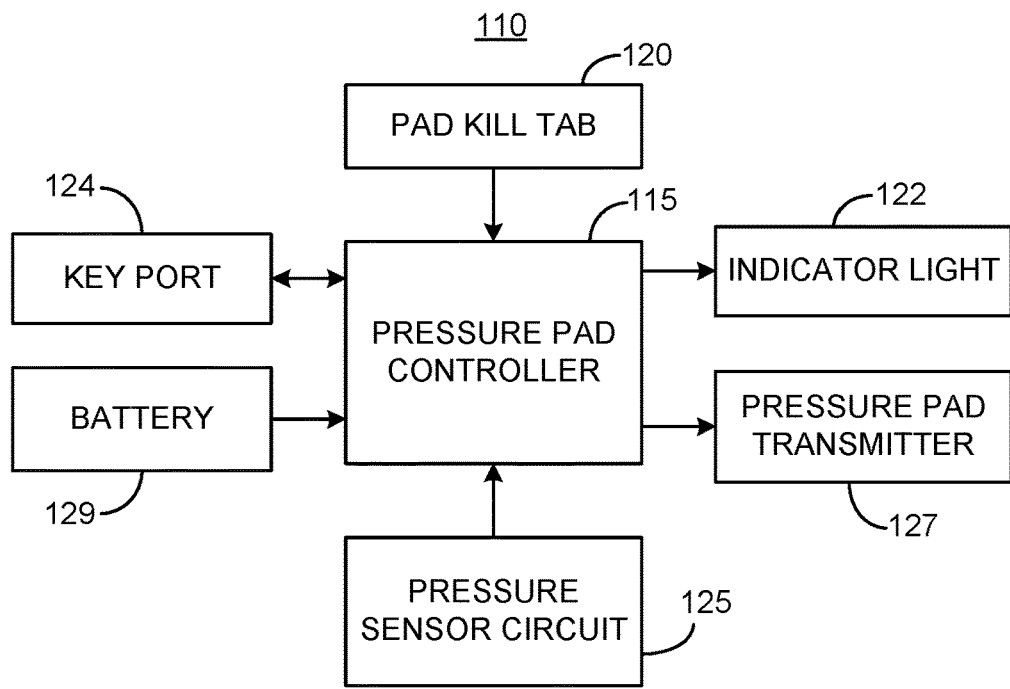
FIG. 9 is a block diagram of a pressure sensor pad electronic circuit of any one of the bed, chair, or toilet pressure sensor pads shown in FIGS. 5-7.
Figure 12:
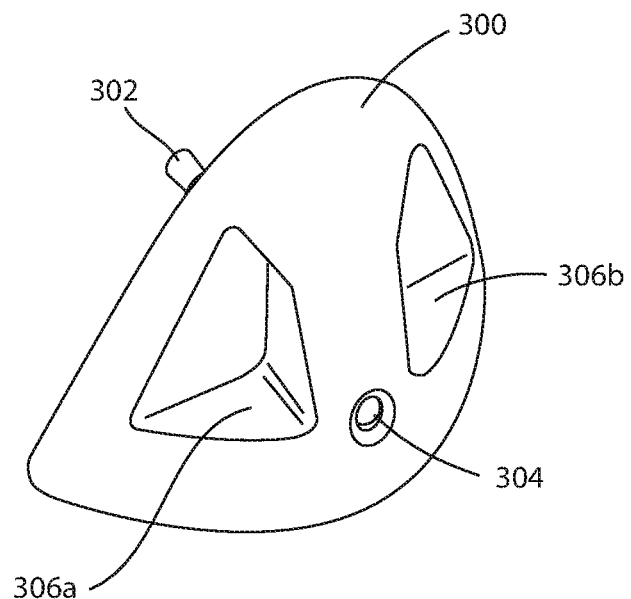
FIG. 12 is a perspective view of the front of an electronic key used in the notification system of FIG. 2.
Figure 13:
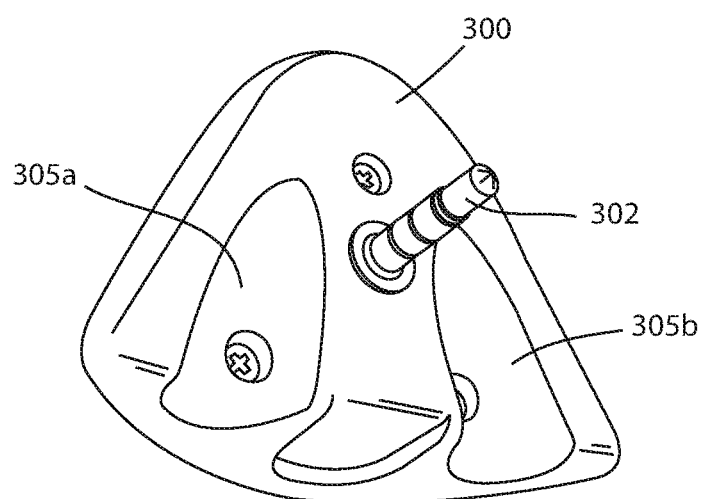
FIG. 13 is a perspective view of the rear of the electronic key shown in FIG. 12.

FIGS. 8A, 8B, and 9 show the structure of an exemplary pressure sensor pad electronic circuit 110 for use in the pressure sensor pads 100. Pressure sensor pad electronic circuit 110 may include a key port 124 for receipt of an electronic key 300 (FIGS. 3, 12, and 13). The electronic key 300 is associated with the monitor 15 and includes a memory device in which is stored a unique monitor identification code identifying the monitor 15. The key port 124 may take any form including a USB receptacle/plug or a micro-USB receptacle/plug. To pair a sensor pad 100 with the monitor 15, the key 300 is removed from the monitor 15 and is plugged into key port 124 of the sensor pad to be activated and paired. The pressure sensor pad electronics circuit 110 in each sensor pad 100 is inactive (in a low power sleep mode) until such time that the key 300 is inserted into the key port 124 of the pressure sensor pad electronic circuit 110. Such insertion wakes up the pressure sensor pad electronics circuit 110 and causes the pressure pad controller 115 to download and store the unique monitor identification code identifying the monitor 15 that is stored in the key 300. Thereafter this causes the pressure pad controller 115 to begin periodically transmitting a signal via a transmitter 127 that includes the downloaded monitor identification (ID) code as well as a status code, which indicates whether the pressure sensor pad 100 is active or inactive. By including the ID code of the monitor 15 in the signals transmitted from the sensor pads 100, any monitor in an adjacent room would ignore those signals and the monitor 15 would only have to monitor signals having its ID code. The pressure sensor pad 100 is active if a pressure sensor circuit 125 is sensing the application of pressure corresponding to that which would be applied if a patient is laying or sitting on the pressure pad 100. The signal will also include a type code, which identifies the type of pressure sensor pad that corresponds to the pressure sensor pad 100. For example, if the pressure sensor pad 100 is a bed pressure sensor pad 100*a*, the type code will identify the sensor pad 100 as a bed pressure sensor pad 100*a*, and if the pressure sensor pad 100 is a chair pressure sensor pad 100*b*, the type code will identify the pad as a chair pressure sensor pad 100*b*, etc.

As an alternative to the pairing method above, the port 124 may be directly connected to a corresponding port on the monitor 15. A hopper cord may also be used to connect the port 124 to the monitor 15. The monitor 15 may then directly wake up the pressure sensor pad electronics circuit 110 and cause the pressure pad controller 115 to download and store the unique monitor identification code identifying the monitor 15. This removes the need for the key 300.

Upon initially receiving the signal from the sensor pad 100, the monitor 15 may play via speaker 65 an audible message that "_____ pad connected" (where the blank would be filled in with the type of sensor pad). For example, if the type code in the received signal indicated that the sensor pad was a bed pressure sensor pad 100*a*, the monitor 15 would announce that "bed pad connected." The monitor 15 may then also announce the active/inactive status of the pressure sensor pad 100, such as "bed pad active." By providing these audible voice messages or a tone, a caretaker may immediately know if the pressure sensor pad is properly paired and operating. Further, a visual indication will be shown that the pad has been connected.

Also upon initially receiving a signal from a sensor pad 100, the monitor 15 may begin monitoring the time that the sensor pad 100 is in service and may subsequently issue a notification that the sensor pad life is about to expire when the service time of that pad reaches a threshold amount of time. Such a notification may be presented at the nursing station monitoring system 8 and/or at the monitor 15.

As shown in FIG. 9, the pressure sensor pad electronic circuit 110 may further include at least one battery 129 and an optional indicator light 122 that may be used to indicate whether the pad 100 is active. In general, however, there should be no need for an indicator light 122 as the status may be more easily obtained from the monitor 15 and eliminating the indicator light also eliminates any added drain on the battery 129. The indicator light 122 may also show remaining battery life.

As stated above, once activated, the pressure sensor pad 100 periodically transmits signals including the monitor ID code, the type code, and the active/inactive status code. The monitor 15 monitors such signals for changes in status. If a signal is received that indicates that a pressure sensor pad 100 is active, the monitor 15 announces that the pad is active as described above and then monitors subsequent signals to determine if a signal includes a status code indicating that the pressure sensor pad 100 is inactive. If a previously active pressure sensor pad 100 becomes inactive, the monitor 15 may take any one or more of the following steps. First, it may await a first predetermined time period (of, for example, 3 seconds) before taking any action, as it is possible the patient just moved on the bed, chair or toilet without getting up in which case the received signals from the sensor pad would resume with a status code indicating that the pad is active with the first predetermined time period. If a subsequent signal with a status code indicating that the pad is active is received within the predetermined time period, the monitor 15 will take no further action. However, if no subsequent signals are received with a status code indicating that the pad is active within the predetermined time period, the monitor 15 may initially play an audible pre-recorded message that may state "John, please do not get up without assistance. If you need assistance please press your nurse call button." The monitor 15 may then await a second predetermined time period, which may be a different amount of time from the first predetermined time period to see if the status code changes back to active, at which point the monitor 15 would take no further action. However, if the status code does not change back to active within the second predetermined time period, the monitor may again play the audible message instructing the patient not to get up and the monitor 15 may further send a notification to the nurse monitoring system 8 at the nursing station 4 or to a mobile communication device 250 to notify the nursing staff that the patient has gotten up without assistance. The caretaker may silence any such notification/alarm upon entering the patient's room 2 by pressing the RESET button 67a on monitor 15.

By knowing the type of pressure sensor pad 100 that is changing from active to inactive status, the monitor 15 may play different audible tones or messages tailored for the particular type of pressure sensor pad and/or take different actions such as immediately notifying a caretaker. For example, if the sensor pad is the bed pressure sensor pad 100a, the monitor 15 may play a message such as "Mary, please remain in your bed. If you need assistance please press your nurse call button." As another example, if the sensor pad is the toilet pressure sensor pad 100c, the monitor 15 may play a message such as "Mary, please remain on the toilet. A nurse is on the way to assist you."

In the event that the monitor 15 notices that a sensor pad 100 has stopped sending its periodic signal for a specified amount of time, the monitor 15 may change the status flag stored therein for the particular sensor pad 100. In this way, if a caretaker presses the STATUS button 67c on the monitor 15, the monitor 15 will announce the connection status of the various sensor pads from which signals are being received. This would allow a caregiver to recognize if, for example, the chair pressure sensor pad 100b, which may be on a wheelchair, has moved out of range of the monitor 15. As another example, a sensor pad may just cease operating properly (such as the battery expiring prematurely), at which point the caretaker pressing the STATUS button 67c would be able to determine which pad is not operating properly and to replace the defective sensor pad. As an additional measure, the monitor 15 may, upon detecting that a sensor pad 100 has stopped sending its periodic signal for a specified amount of time, treat the lack of the periodic signal as if the sensor pad went inactive and take the steps noted above, at which point the caretaker would eventually be notified that the patient may have gotten up. Upon entering the patient's room, the caretaker would then see that the patient had not gotten up and immediately be able to determine that the sensor pad on which the patient is resting may not be operating properly or is no longer present in the room. The caretaker could then verify this by pressing the STATUS button 67c and listening to the status of each sensor pad that is connected. The lost sensor pad 100 may then be cleared by being unpaired by, for example, pressing a combination of two of the buttons on the monitor 15.

Although the status of the sensor pads 100 is stored in monitor 15 based on the periodic signals received from the sensor pads, the controller 70 may alternatively or additionally be configured to transmit a status request signal to each of the sensor pads upon sensing that the STATUS button 67c is pressed to obtain an updated status of each sensor pad.

In addition to audibly announcing the status of each sensor pad 100, the monitor 15 may illuminate indicator lights 78a, 78b, 78c, 78d, and 78e to indicate the status. For example, the monitor 15 may cause such indicator lights to illuminate if there is an ongoing connection with the corresponding sensor pad and may cause such indicator lights to be extinguished if there is no ongoing connection with the corresponding sensor pad. Alternatively the color of light emitted may be changed to indicate the status. These lights may be illuminated/extinguished continuously or only when the STATUS button 67c is pressed. Further, the monitor 15 may be configured to show the status using the indicator lights 78 when the STATUS button 67c is pressed and if the STATUS button 67c is pressed and held for a certain time, the monitor 15 may announce which sensor pads are connected followed by an announcement of which pad is active. Note that the indicator lights may be also be used to show the active sensor pad by keeping that indicator light illuminated for 3 seconds, for example, after the others are extinguished or by using a different color or by flashing. A single press of the STATUS button 67c may show a visual representation of the pads that are connected and the pad that is active. A double press of STATUS button 67c may have the monitor 15 announce which sensor pads are connected followed by an announcement of which pad is active. Pressing and holding of the STATUS button 67c will provide the local alarm tones. This feature identifies the mode selected on the back of the monitor by playing the tones that are associated with that mode. This could be a single pressure tone, a single incontinence tone, or a combination of the two. This feature prevents the caregiver from having to remove the monitor from the mount to see what mode is selected. Also, a caregiver can press the STATUS button 67c to see if a pad connection has been lost. If a pad is lost, an indicator light on the monitor 15 will continue to blink until the pad connection is reestablished, or until the pad is disconnected from the monitor.

The HOLD button 67b on monitor 15 allows a caretaker to assist the patient for a certain period of time without causing any notifications or alarms if it is subsequently detected that an active sensor pad is no longer active. For example, if a caretaker wishes to assist a patient from the bed to a chair or toilet, the caretaker presses the HOLD button 67b on the monitor 15. The monitor 15 will then hold for a predetermined time of, for example 30 seconds, so that it does not alarm for this predetermined time. Such time period should be sufficient to allow a patient to be moved from the bed to the bathroom or chair at which point the respective toilet pressure sensor pad 100c or chair pressure sensor pad 100b becomes active thereby preventing any alarms. When the HOLD button 67b is pressed, the monitor 15 may audibly announce that "monitor will hold for 30 seconds." The monitor 15 may then stay silent or periodically beep and may then state "10 seconds until reset" as the hold time progresses and then may state "reset" at the expiration of the hold period. If pressure is reapplied to the pad at the end of the 30 second hold, the monitor will produce a tone that will indicate that the pad is automatically reactivated. This tone confirms that the pad is active after the hold. If pressure is not reapplied, the pad is not active and the monitor will not produce the notification tone.

The monitor 15 may also be configured such that upon pressing and holding the HOLD button 67b, the monitor 15 may hold for a longer period of time, such as 5 minutes. This extended hold period is useful when an incontinence event has occurred. For example, if an incontinence sensor pad 100d senses the presence of moisture, it signals the monitor 15, which responds by notifying a caretaker. The caretaker would then press and hold the HOLD button 67b upon entering the room. The monitor 15 would then state "incontinence alarm will hold for 5 minutes," for example, and start a 5 minute timer. This time period may be a time other than 5 minutes, but should be of sufficient length of time for the caregiver to move the patient to a chair or toilet, change the sheets, terminate the wet incontinence sensor pad 100d by pulling the associated kill tab 120 (FIGS. 8A and 8B), and install and activate a new incontinence sensor pad 100d (using the key 300). This 5 minute hold would not prevent any alarms or notifications from being generated by monitor 15 pertaining to any pressure sensor pads. However, if the caretaker is moving the patient, the caretaker may press the HOLD button 67b to initiate a 30 second hold that prevents any alarms from the monitor in response to the pressure sensor pads and then move the patient. The caretaker may then press hold again for the 30 second monitor hold to move the patient back to the bed (or chair if that is where the incontinence event occurred). Another approach is that the caretaker could otherwise just use the 30 second hold to move the patient and could silence any alarm indefinitely by pulling the kill tab on the wet incontinence sensor pad 100d. The hold on the incontinence alarm would then be indefinite until such time that a new incontinence sensor pad 100d is activated and paired with the monitor 15.

The incontinence pad can also be silenced by simply unclipping the quick connect 470, 470' from the pad or diaper. When the pad or diaper is removed, the incontinence alarm will stop. Also, if the incontinence alarm is sounding, the nurse can press the HOLD button and the monitor will automatically select the incontinence hold over the pressure hold. Normally, a single press of the HOLD button will activate the pressure hold. The monitor may switch from a press and hold requirement for the incontinence hold, to a single press when the incontinence alarm is sounding.

Figure 10:
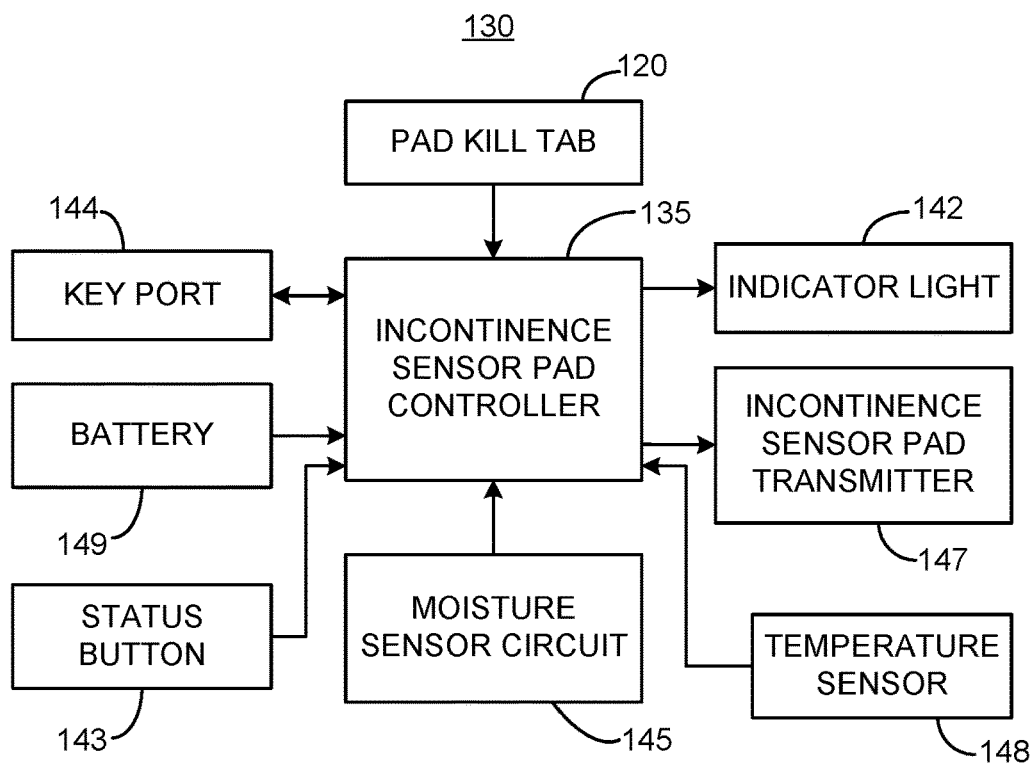
FIG. 10 is a block diagram of an electronic circuit of an incontinence sensor pad or quick connector for an incontinence sensor pad used in the notification system of FIG. 2.

FIG. 10 shows an example of the structure of an exemplary electronic circuit 130 for use in the incontinence sensor pad 100d or in a quick connector module 470, 470' (FIGS. 19-22 and 24-27). A key port 144 may be provided for receipt of electronic key 300 (FIGS. 3, 12, and 13). Similar to the pairing process noted above with respect to pressure sensor pads, to pair an incontinence sensor pad 100d with the monitor 15, the key 300 is removed from the monitor 15 and is plugged into key port 144 of the incontinence sensor pad 100d to be activated and paired. The incontinence sensor pad electronics circuit 130 in the incontinence sensor pad 100d is inactive (in a low power sleep mode) until such time that the key 300 is inserted into the key port 144 of the incontinence sensor pad electronic circuit 130. Such insertion wakes up the incontinence sensor pad electronics circuit 130 and causes the incontinence pad controller 135 to download and store the unique monitor identification code identifying the monitor 15 that is stored in the key 300. Thereafter this causes the incontinence pad controller 135 to begin periodically transmitting a signal via a transmitter 147 that includes the downloaded monitor identification code as well as a status code, which indicates whether the incontinence sensor pad 100 is dry or wet. By including the ID code of the monitor 15 in the signals transmitted from the incontinence sensor pad 100d, any monitor in an adjacent room would ignore those signals and the monitor 15 would only have to monitor signals having its ID code. A moisture sensor circuit 145 is connected to controller 135 to indicate whether the sensor pad 100d is wet or dry. The periodic signal will also include a type code, which identifies the type of sensor pad as an incontinence sensor pad 100d. Again, it is possible to use a different pairing method without requiring the key 300 such as by connecting the electronic circuit 130 directly to the monitor 15 or using a cord.

Upon initially receiving the signal from the incontinence sensor pad 100d, the monitor 15 will play via speaker 65 an audible message that "incontinence pad connected." The monitor 15 may then also announce the wet/dry status of the incontinence sensor pad 100d, such as "incontinence pad is dry." By providing these audible voice messages or a tone, a caretaker may immediately know if the incontinence sensor pad is properly paired and operating.

Also upon initially receiving a signal from the incontinence sensor pad 100d, the monitor 15 may begin monitoring the time that the incontinence sensor pad is in service and may subsequently issue a notification that the incontinence sensor pad life is about to expire when the service time of that pad reaches a threshold amount of time. Such a notification may be presented at the nursing station monitoring system 8, mobile communication device 250, and/or monitor 15.

As shown in FIG. 10, the electronic circuit 130 may further include at least one battery 149 and an optional indicator light 142 that may be used to indicate whether the pad 100d is active. In general, however, there should be no need for an indicator light 142 as the status may be more easily obtained from the monitor 15 and eliminating the indicator light also eliminates any added drain on the battery 149. As explained further below, electronic circuit 130 may further include a status button 492' that when pressed causes the indicator light 142 to display a status wherein the status may include whether the electronic circuit is properly electrically coupled to the sensor pad 100d. The status indicator 142 may further indicates a status when there is an incontinence event.

FIGS. 12 and 13 show an example of the key 300. As shown, key 300 includes a plug 302 that may be, for example, an ⅛ inch diameter pin, that is configured to plug into key port 82 of monitor 15, key port 124 of sensor pads 100, key port 144 of incontinence sensor pad 100d, and key port 164 or nurse call relay device 200. Note, however, that the plug 302 may alternatively be a USB or micro-USB plug. Key 300 also includes a memory device in which the monitor ID may be stored and may include an optional indicator light 304. The indicator light 304 may be used to indicate the status of the pairing operation when the key 300 is inserted into a key port. For example, the indicator light 304 may blink during a pairing operation and remain on constantly once the pairing is complete. Alternative, the indicator light 304 may change color.

The body of key 300 may include one or more detents 306a and 306b to facilitate gripping of the key 300 by a user so that it may be readily pulled from a key port. The body may further include two or more recesses 305a and 305b to receive corresponding protruding portions of housing 20 of monitor 15 proximate the illumination lights 84.

Although a particular configuration of key 300 is shown, the key 300 may take various forms and may include a USB memory stick or a similar portable memory device. Further, in some of the embodiments described herein, key 300 may not be included as it may also be possible to pair sensor pads 100a-100d by directly connecting a terminal thereon to a terminal on the monitor 15. Further, pairing may be performed wirelessly by entering each in a pairing mode at the same time and in proximity to one another.

Figure 11:
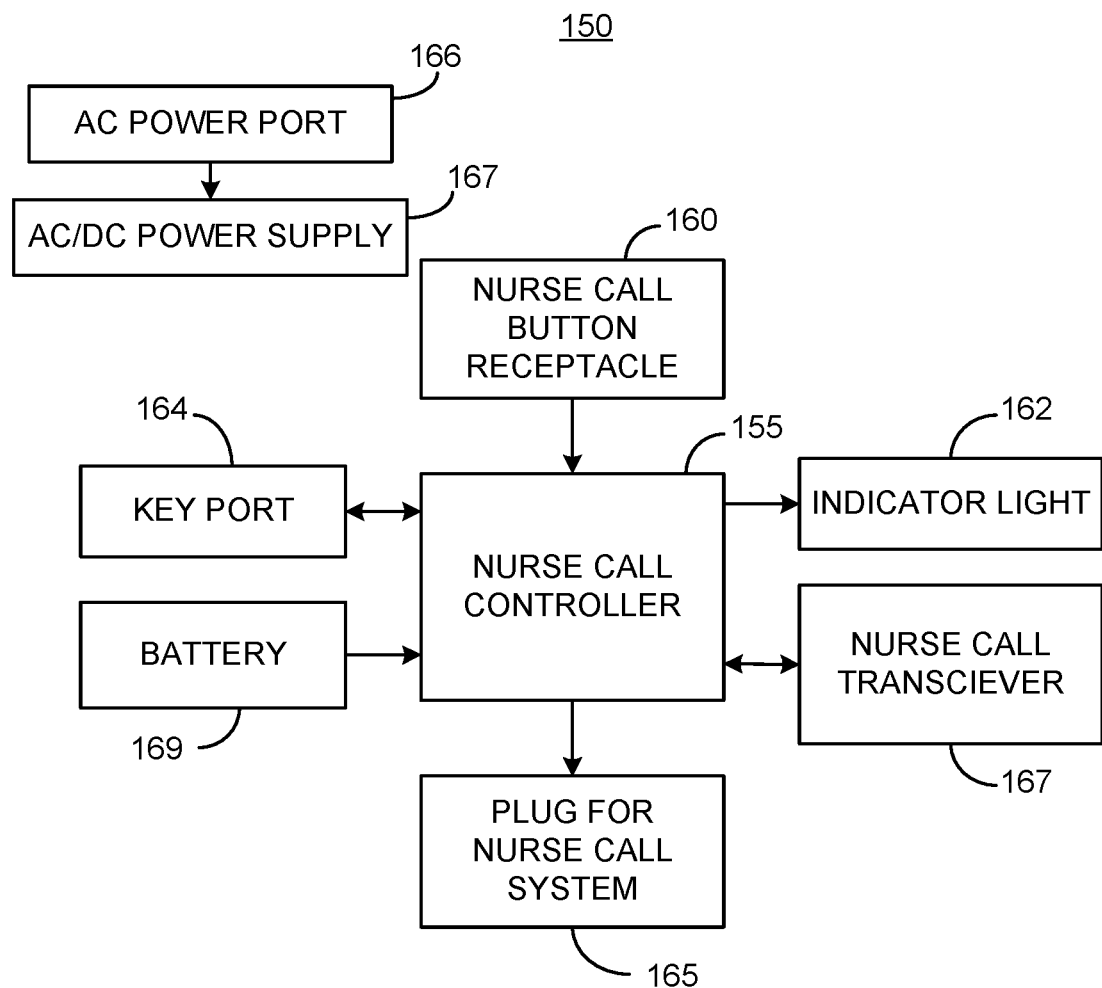
FIG. 11 is a block diagram of a nurse call electronic circuit of a relay device used in the notification system of FIG. 2.
Figure 14:
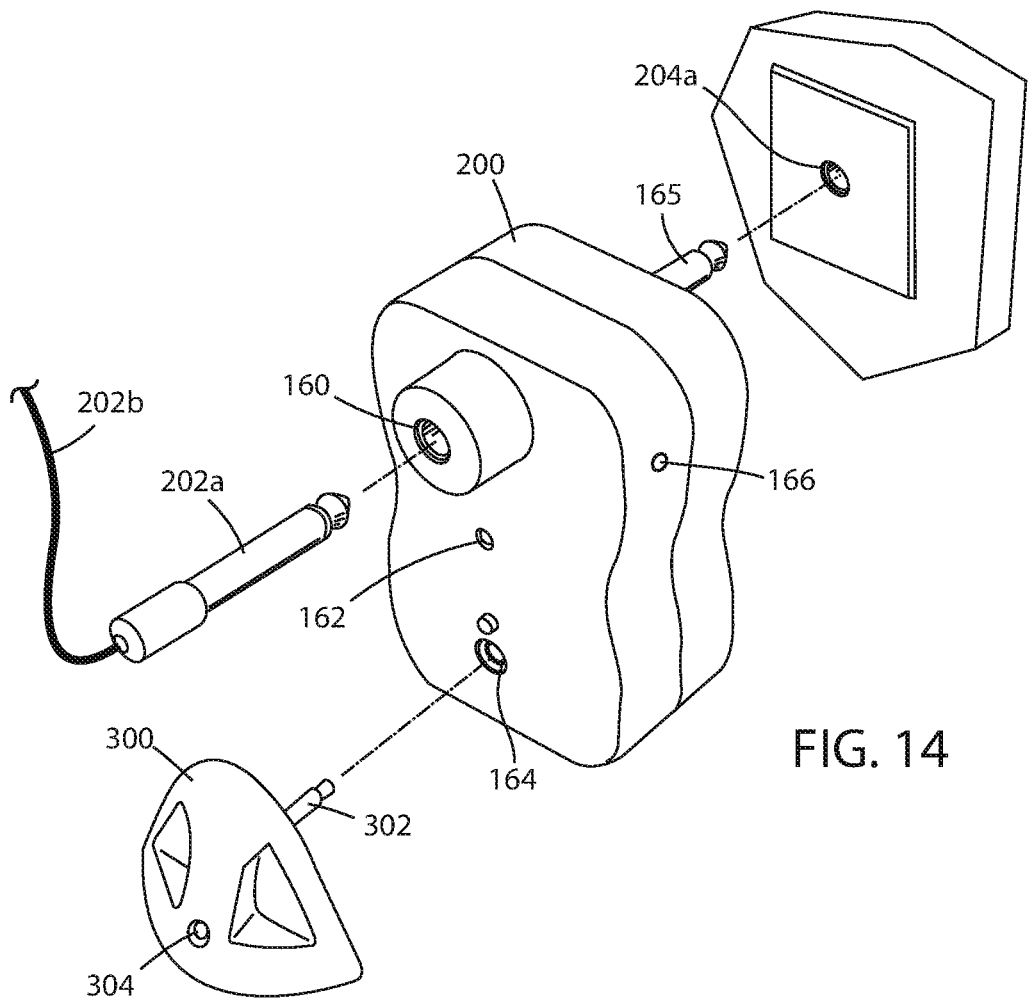
FIG. 14 is a perspective view of the front of the nurse call relay device used in the notification system of FIG. 2.
Figure 15:
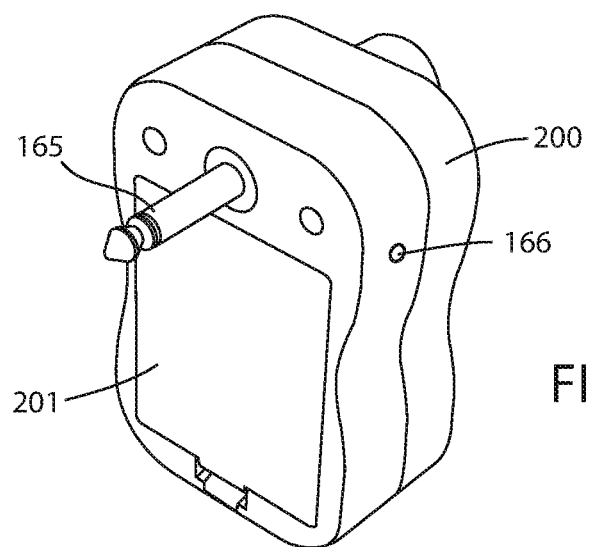
FIG. 15 is a perspective view of the rear of the nurse call relay device shown in FIG. 14.

FIGS. 14 and 15 show an example of the nurse call relay device 200. FIG. 11 shows the electronics 150 within the nurse call relay device 200. Nurse call relay device 200 includes a nurse call button receptacle 160 for receiving a plug 202a of a nurse call button 202 (FIG. 1), which is connected to the actual nurse call button via a wire 202b. Nurse call relay device 200 further includes a plug 165 for plugging into a wall receptacle 204a of a pre-existing nurse call system 204 (FIG. 1). Plugs 202a and 165 may be ¼ inch monojack plugs. As shown in FIG. 11, the electronics 150 include a nurse call controller 155 that communicates with both the nurse call button receptacle 160 and the plug 165 such that controller 155 may pass through any nurse call signal received from nurse call button 202 to the nurse call system 204. Controller 155 may further transmit other information over the nurse call system 204 via its connection to plug 165 and wall receptacle 204a. Although plug 165 is shown as being in a fixed orientation relative to the body of the nurse call relay device 200, it may be configured in a pivotable arrangement so that it can be selectively pivoted to extend out of the back, top, or out of the side of the body of the nurse call relay device 200. Alternatively, the plug 165 may be a port and the connection to wall receptacle 204a may be via a hopper cord.

Nurse call relay device 200 may further include a key port 164 for receiving plug 302 of key 300. Nurse call relay device 200 may remain in a sleep state until such time that controller 155 detects the presence of the key plug 302 in key port 164. Upon detecting the presence of the key plug 302 in key port 164, the controller 155 may retrieve and store the monitor ID stored in the memory device of key 300. This allows the nurse call relay device 200 to be paired with the monitor 15 and thereby only respond to signals from the monitor 15 having that unique monitor ID. The controller 155 may then begin transmitting a periodic signal to monitor 15 using a nurse call transceiver 167. This periodic signal would include the monitor ID as well as a status code and a type code identifying the periodic signal as coming from a nurse call relay device. The status code may indicate a status of at least one battery 169 that is powering the nurse call relay device 200. Nurse call relay device 200 may also include an optional indicator light 162 to visibly indicate a status. Again, it is possible to use a different pairing method without requiring the key 300 such as by connecting the electronic circuit 150 directly to the monitor 15 or using a cord.

In addition to sending the periodic signals to the monitor 15, the transceiver 167 may also receive signals from the monitor 15. For example, as discussed above, the monitor 15 may transmit signals to the nurse call relay device 200 to cause nurse call relay device 200 to transmit an alarm or other notification signal to the nurse call/monitoring system 8 at the nursing station 4. Additionally, other data may be transmitted from monitor 15 for transmission to the nursing station 4, such as the historical data as discussed above. Nurse call relay device 200 may be configured to transmit an acknowledgement signal back to monitor 15 to acknowledge receipt of any such data or alarm/notification signals.

It is also possible that information may be transmitted to the nurse call relay device 200 from the nurse call/monitoring system 8 for relaying to monitor 15. For example, an alarm may be silenced or a status request may be sent from the nurse call/monitoring system 8. Status information may then be sent back from the monitor 15. Further, video may be streamed to/from the monitor 15 as discussed above.

Referring back to FIG. 15, the nurse call relay device 200 may include a battery compartment 201 for storing at least one battery 169 used to power the nurse call relay device. It will be appreciated, however, that the nurse call relay device 200 may alternatively be powered by AC power provided from the hospital room using AC power port 166. As shown in FIG. 11, the nurse call relay device 200 may also include an AC/DC converter power supply 167.

Figure 16:
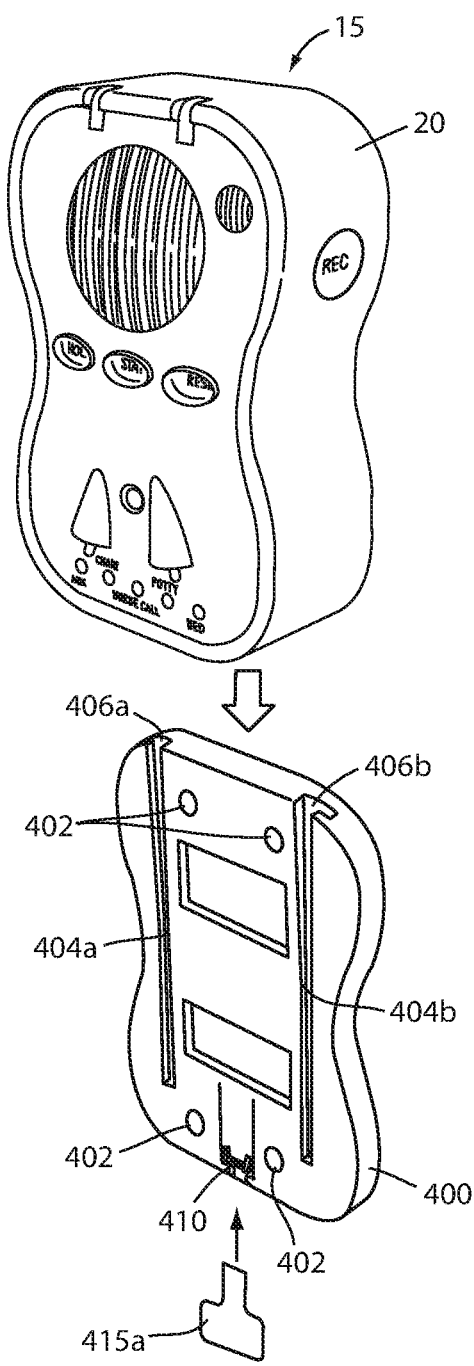
FIG. 16 is a perspective view of the front of the monitor shown in FIG. 3 and the front of a mounting plate.

FIGS. 16 and 17 show an example of a mounting system for mounting a monitor 15 to a wall such that the monitor 15 may not be removed from the wall without a specific tool such as wall mount key 415a. As shown, a mounting plate 400 is provided that may be screwed into a wall via screws passing through holes 402 of mounting plate 400. In FIG. 16, the front of mounting plate 400 is shown in which two vertical slots 404a and 404b are formed that extend upwards to openings 406a and 406b, respectively in the upper edge of mounting plate 400. FIG. 17 shows the backs of monitor 15 and mounting plate 400. As shown, the back of monitor 15 includes a pair of parallel L-shaped flanges 408a and 408b that extend vertically and are spaced apart by the same distance as vertical slots 404a and 404b on the front of mounting plate 400. Each of the flanges 408a and 408b protrude rearwardly and has a lateral leg that extends laterally away from the lateral leg of the other flange. The slot openings 406a and 406b on the top edge of mounting plate 400 are shaped to correspond to the profile of flanges 408a and 408b such that monitor 15 may be slid downward for mounting to mounting plate 400. When the lowermost portion of flanges 408a and 408b reaches the bottom of slots 404a and 404b, respectively, the monitor 15 cannot be moved farther down, and a catch 410 on mounting plate 400 locks into an opening 412 on the back of monitor 15 to prevent the monitor 15 from being slid upwards. In this way, monitor 15 may not be removed and tampered with. A special wall mount key 415 may be required to slide up between the mounting plate 400 and monitor 15 to engage the catch 410 to allow the monitor 15 to be slid upwards and removed. As also shown in FIG. 17, a battery door 414 and associated catch 415 may be provided at the back of the monitor 15 for allowing access to the battery compartment where the at least one battery 50 is stored. By placing the battery compartment at the back of the monitor, access to the battery compartment may be limited to those that have the special tool for removing the monitor 15 from the mounting plate 400.

Figure 18A:
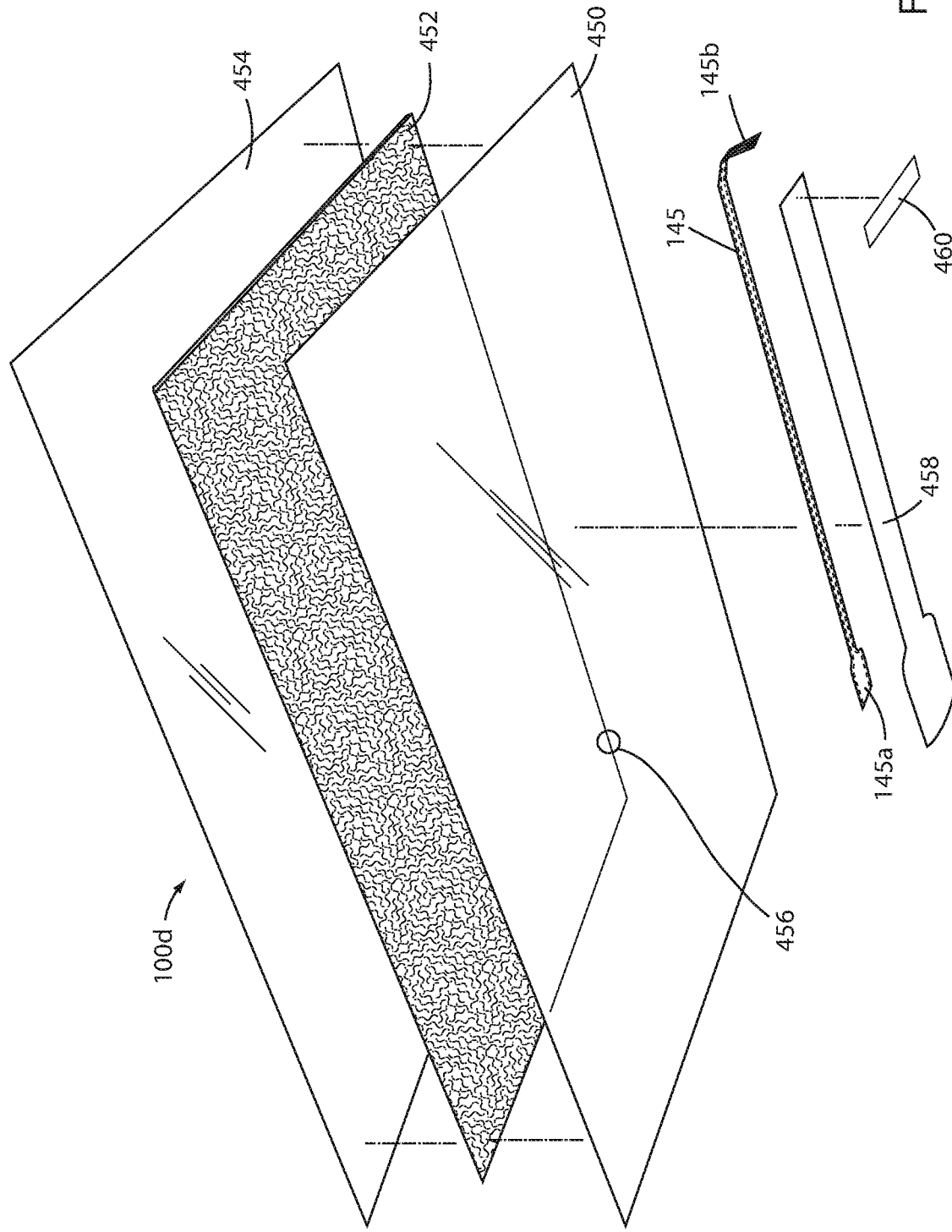
FIG. 18A is an exploded perspective view of a first example of an incontinence sensor pad used in the notification system of FIG. 3.

FIG. 18A shows a first example of the construction of an incontinence sensor pad 100d. The pad may include a moisture-impervious substrate 450 that extends the entire bottom surface of the pad 100d, a moisture absorption pad 452 that lies over the moisture-impervious substrate 450, and a moisture-permeable substrate 454 that lies over the moisture absorption pad 452. The two substrates 450 and 454 and absorption pad 452 together form an absorption chuck for absorbing urine or other fluids and thereby impeding the flow of such fluids to a mattress or chair. The incontinence sensor pad 100d may further include a moisture sensor circuit 145 that may be formed of a thin substrate with two conductive tracings extending from a sensing end 145a of the substrate to a connecting end 145b. The sensing end 145a is positioned under an aperture 456 formed in bottom moisture-impermeable substrate 450 where any fluids may be detected upon absorption by pad 452. Such fluids are electrically conductive and bridge the gap between the electrically conductive tracings moisture sensor circuit 145. An adhesive strip 458 is used to hold the moisture sensor circuit 145 in place on the bottom of moisture-impermeable substrate 450. An additional adhesive strip 460 may be used to firmly secure the connecting end 145b of moisture sensor circuit 145 to the substrate 450.

Figure 18B:
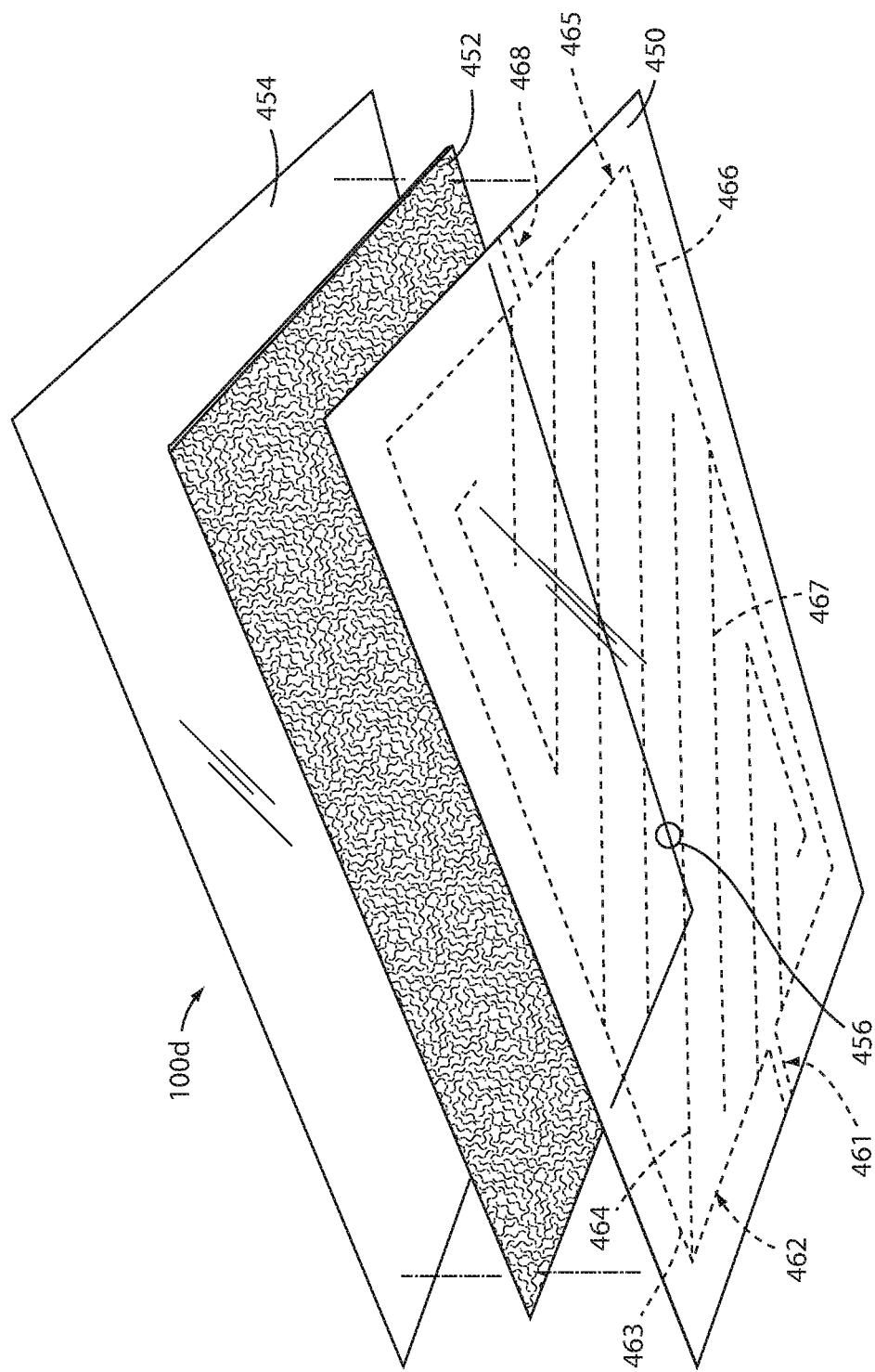
FIG. 18B is an exploded perspective view of a second example of an incontinence sensor pad used in the notification system of FIG. 3.

FIG. 18B shows a second example of the construction of an incontinence sensor pad 100d. All the components of the sensor pad 100d are the same as in FIG. 18A with the exception that the moisture sensor circuit 145, adhesive strip 458, and additional adhesive strip 460 are not used in the second example. Instead, the inward-facing side of moisture-impervious substrate 450 has a first electrically conductive tracing 462 on the inner surface of the substrate 450. The first electrically conductive tracing 462 includes a first conductive bus 463 connected to a first plurality of interdigitated conductive extensions 464. The first conductive bus 463 extends to a first terminal portion 461 of the inner surface of substrate 450. A second electrically conductive tracing 465 is also provided on the inner surface of the substrate 450. The second electrically conductive tracing 465 includes a second conductive bus 466 connected to a second plurality of interdigitated conductive extensions 467. The second conductive bus extends to the first terminal portion 461 of the inner surface of substrate 450. The first and second conductive buses 463 and 466 extend in parallel a predetermined distance from the first terminal portion 461 of the surface of substrate 450. Note that the substrate 450 may be larger than the substrate 452 and substrate 454 to facilitate coupling of the electronic module 130.

Figure 28A:
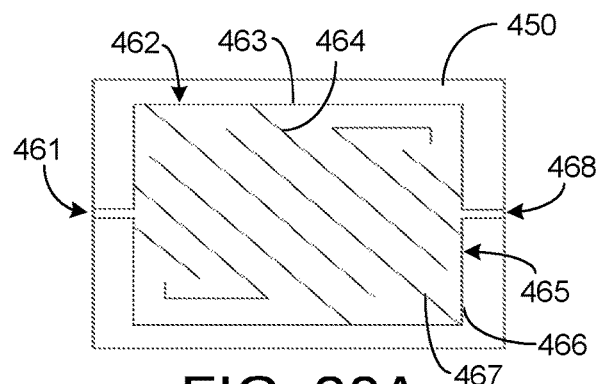
FIGS. 28A-28M are various examples of configurations of conductive tracings that may be used on the incontinence sensor pad shown in FIG. 18B.
Figure 28B:
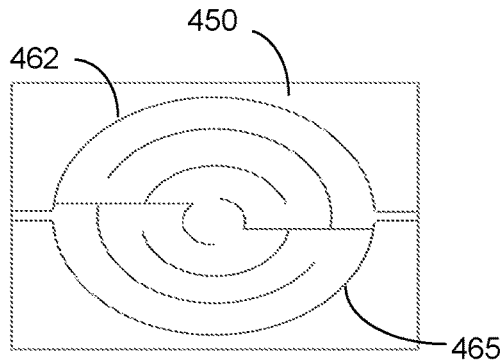
Figure 28C:
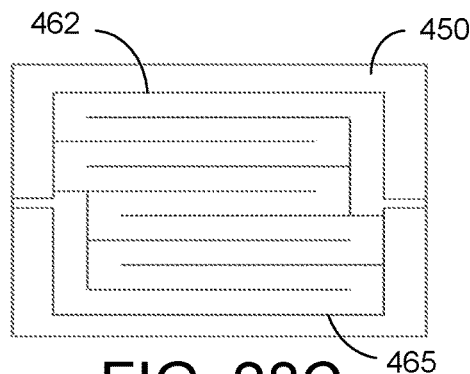
Figure 28D:
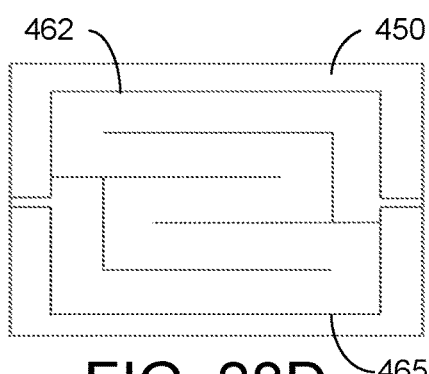
Figure 28E:
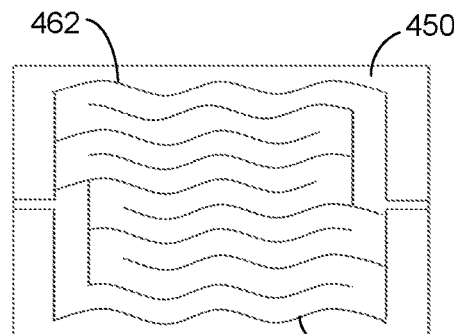
Figure 28F:
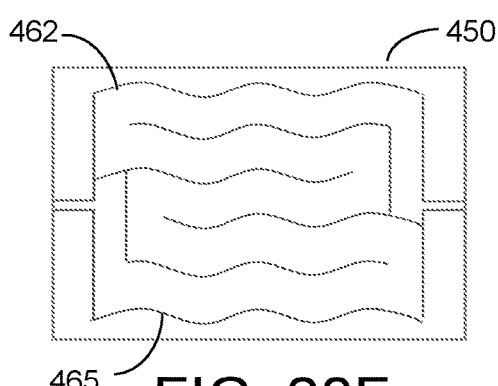
Figure 28G:
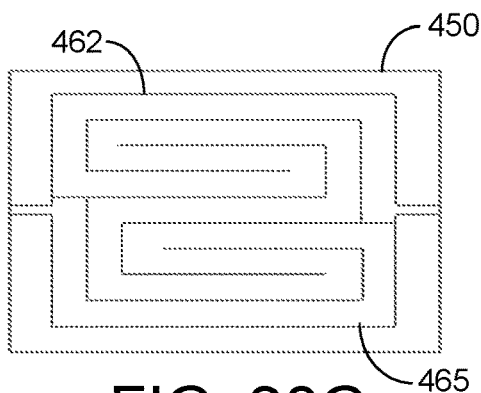
Figure 28H:
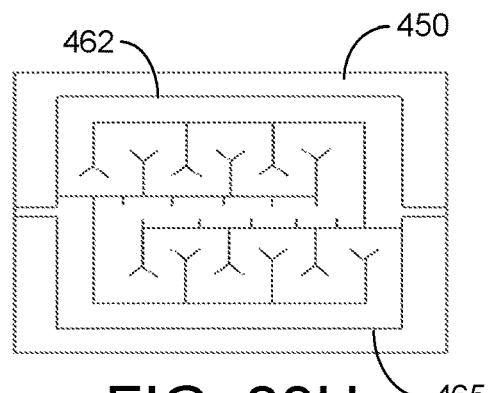
Figure 28I:
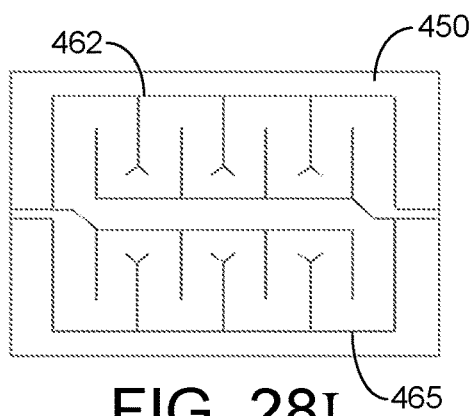
Figure 28J:
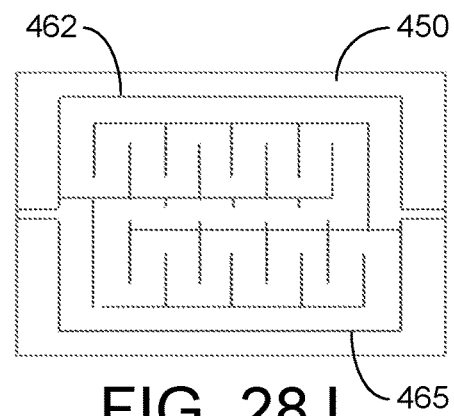
Figure 28K:
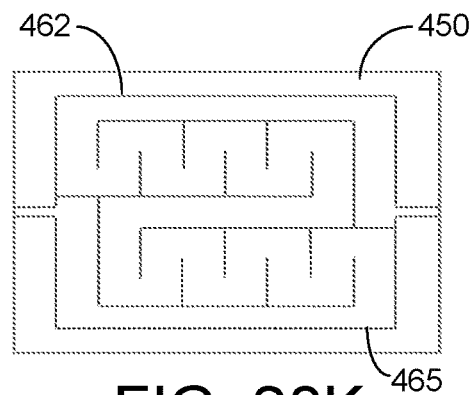
Figure 28L:
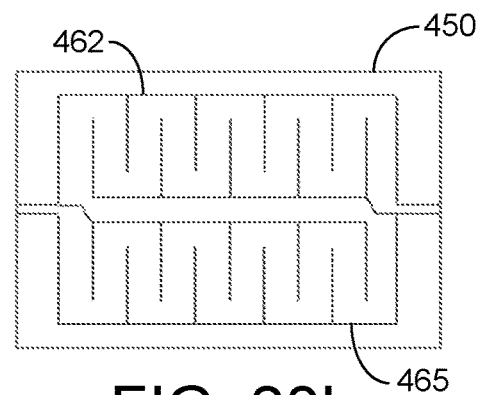
Figure 28M:
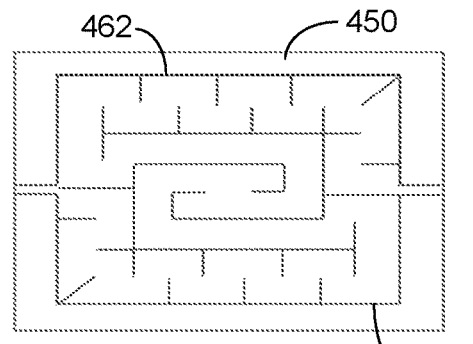
Figure 29:
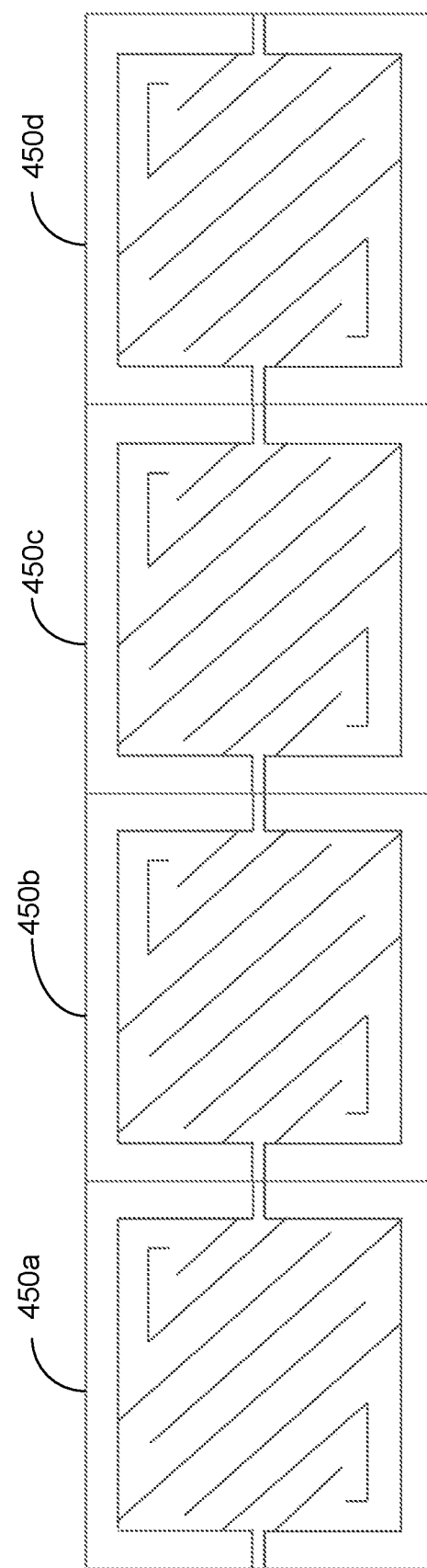
FIG. 29 is a top view of a roll of a substrate with conductive tracings printed thereon from which substrates are cut for use in the incontinence sensor pad shown in FIG. 18B.

As also shown in FIGS. 28A and 29, the first and second conductive buses 463 and 466 extend in parallel a second predetermined distance from a second terminal portion 468 of the surface to create an optional second connection location for the electronic module 130.

The incontinence sensor pad 100d is generally rectangular and the second terminal portion 468 of the surface is proximate an opposite side of the incontinence sensor pad from the first terminal portion 461. The generally rectangular incontinence sensor pad 100d includes first, second, third, and fourth sides, wherein the first and third sides are shorter than the second and fourth sides. The first terminal portion 461 is near the first side and the second terminal portion 168 is near the third side. Alternatively, the first terminal portion 461 of the surface may be near the second side and the second terminal portion 468 may be near the fourth side.

A first portion of the first conductive bus 463 that extends to the first terminal portion 161 is co-linear with a second portion of the first conductive bus 463 that extends to the second terminal portion 468, and a first portion of the second conductive bus 466 that extends to the first terminal portion 461 is co-linear with a second portion of the second conductive bus 466 that extends to the second terminal portion 468. The benefit of this feature is that the conductive ink may be printed on a roll of the substrate 450 as shown in FIG. 29 and subsequently cut into separate sheets. By having the conductive buses 463 and 466 extend in parallel for a distance from each edge, there is a greater manufacturing tolerance for where the cut is made in the roll while still ensuring an adequate location to connect the electronics module 130.

Figure 19:
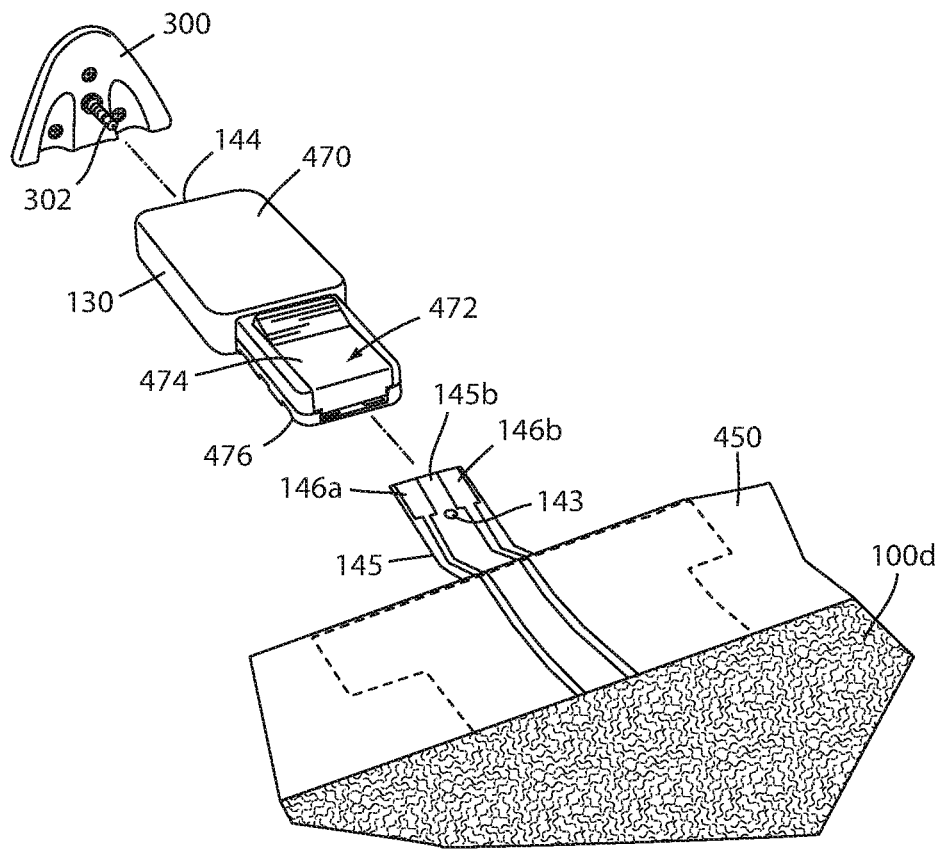
FIG. 19 is a close-up perspective view of the terminal end of the incontinence sensor pad, the electronic key, and a wireless module that connects to the terminal end of the incontinence sensor pad shown in FIG. 18.
Figure 20:
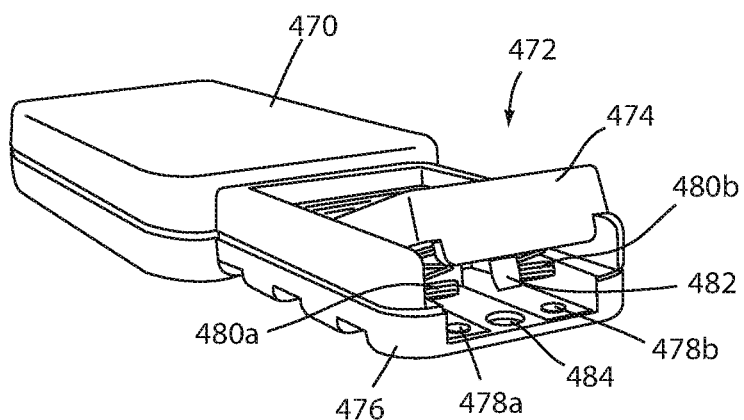
FIG. 20 is a perspective view of the wireless module shown in FIG. 19.

FIGS. 19-23 show two different examples of ways to communicatively couple an incontinence pad 100d to monitor 15. FIGS. 19 and 20 show the use of an incontinence sensor pad electronics circuit 130 such as that shown in FIG. 10 as a means for wirelessly communicating with monitor 15. The incontinence sensor pad electronics circuit 130 may be housed in a wireless module 470 that includes a clip connector 472 for clipping to the connecting end 145b of moisture sensor circuit 145. Clip connector 472 includes a pivoting portion 474 that moves into and out of engagement with a stationary portion 476 so as to receive and lock in place the connector end 145b therebetween. Stationary portion 476 includes two electrically conductive terminals 478a and 478b for electrically coupling to respective conductive pads 146a and 146b of the connector end 145b of moisture sensor circuit 145. Pivoting portion 474 may include a pair of springs 480a and 480b for biasing the connector end 145b against the respective electrically conductive terminals 478a and 478b. The pivoting portion 474 may include a prong 482 that passes through a registration hole 143 in the connector end 145b of moisture sensor circuit 145 and a recess 484 in stationary portion 476. Although not shown in FIGS. 19 and 20, a kill tab 120 may be provided. Also, the wireless module 470 may include a key port 144 for receiving the plug 302 of a key 300.

FIGS. 21-23 show an example of a wired connection of an incontinence sensor pad 100d to monitor 15. A wired module 500 may be provided having a clip connector 472 for clipping to the connecting end 145b of moisture sensor circuit 145. The clip connector 472 may have a pivoting portion 474 and a stationary portion 476 similar to that in the example shown in FIGS. 19 and 20. Wired module 500 differs from wireless module 470 in that it does not include the incontinence sensor pad electronics circuit 130. Instead, wired module 500 simply provides a connection to wires 502 that connects directly to monitor 15 via a releasable clip 504 and sensor port 79 (FIG. 23). In this arrangement, neither incontinence sensor pad 100d nor wired module 500 need include its own controller, but rather the moisture sensor circuit 145 may be wired right into the monitor controller 70.

FIGS. 24-27 show an example of a wireless module 470' that may be connected to the terminal end 461 or 468 of the incontinence sensor pad 100d shown in FIGS. 18A and 18B.

Wireless module 470' includes a clip connector 472' for clipping to the terminal end 461 or 468 to make electrical contact with the conductive tracings 462 and 465. Clip connector 472' includes a pivoting portion 474' that pivots about a pivot point 475' and moves into and out of engagement with a stationary portion 476' so as to receive and lock in place the terminal end 461 or 468 therebetween. Stationary portion 476' includes electrically conductive terminals 477' for electrically coupling to respective conductive buses 463 and 466 at the terminal end 461 or 468. A locking mechanism is provided including a lock tab 490' and a locking pin 492a' that slides in and out of engagement with an extension piece 474a' of the pivoting portion 474' to prevent the pivoting portion 474' from moving from the clipped position. Further, a status button 492' may be provided that when pressed causes the indictor light 142 to illuminate and thereby indicate a status. The indicator light 142 may be located on the stationary portion 476' underneath the pivoting portion 474' provided the pivoting portion 474' is either transparent or has a transparent window or opening above the indicator light 142. Although not shown, the wireless module 470' may include a key port for receiving the plug of a key, such as key 300.

The quick connect incontinence electronic modules 470, 470' may have pins that penetrate the conductive ink material when the quick connect module is attached to the incontinence pad 100d. More specifically, a cloth material may be disposed on top of the conductive ink. In this case, it is desirable to penetrate the cloth material and the ink material with the pins to form a solid connection between the quick connect module and the conductive ink. The quick connect modules may include a spring-loaded ring that surrounds the pins when the quick connect is not in the locked position. This prevents the pins from puncturing the material prematurely, being a hazard when the quick connect is open, and creating a solid connection until after the quick connect is in the locked position.

The incontinence electronic module 130, 470, 470' may include an attachment member on a bottom surface for engaging a surface of the incontinence sensing pad 100d. This helps ensure that the module remains clipped. The attachment member may be a hook and loop-type fastener such as Velcro®, or any other mechanism.

The incontinence electronic module 130, 470, 470' or the sensor pad 100d may also include a temperature sensor 148 (FIG. 10) for sensing the temperature of a patient lying on the incontinence sensor pad 100d, the controller 135 generating a bed sore advance warning signal when the temperature sensed by the temperature sensor 148 reaches a threshold temperature.

FIGS. 28A-28M show a number of different examples of conductive tracings 462 and 465 provided on the substrate 450 of the incontinence sensor pad 100d. It will be appreciated that many other patterns may be used for the conductive tracings.

Figure 30A:
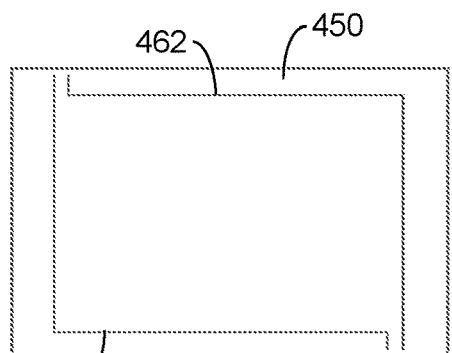
FIGS. 30A-30T are various examples of configurations of conductive buses of conductive tracings that may be used on the incontinence sensor pad shown in FIG. 18B.
Figure 30B:
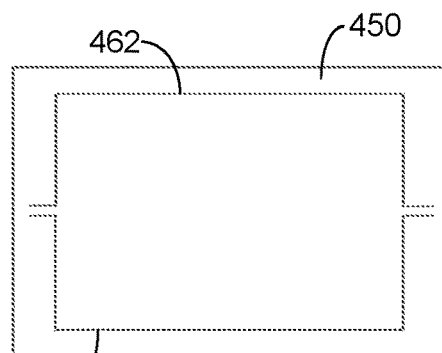
Figure 30C:
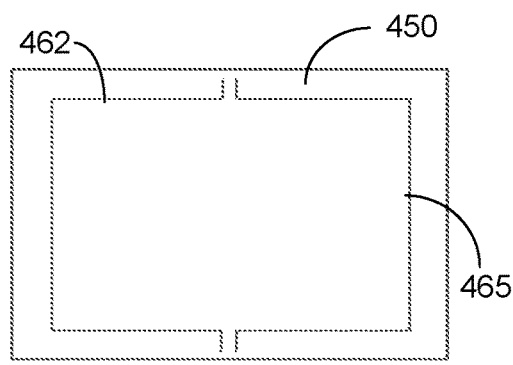
Figure 30D:
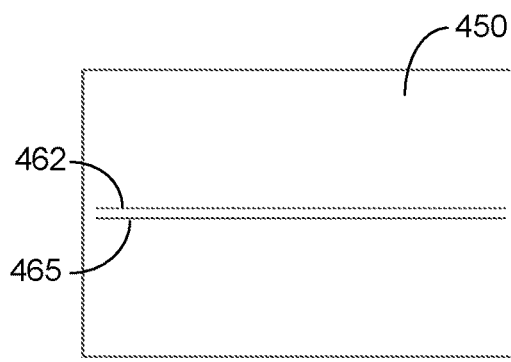
Figure 30E:
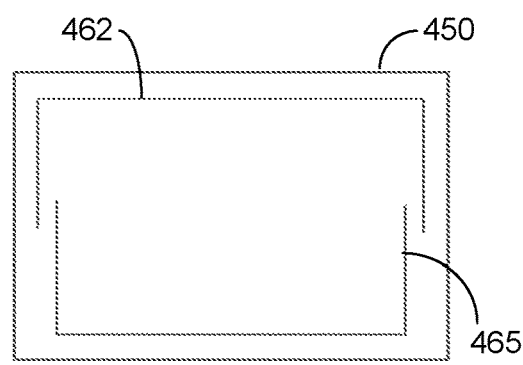
Figure 30F:
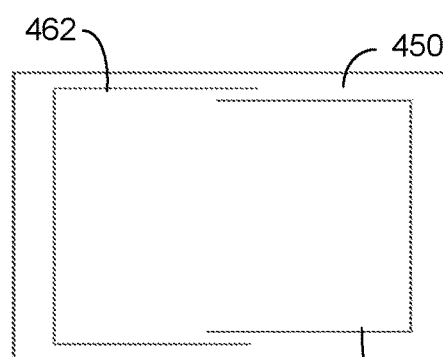
Figure 30G:
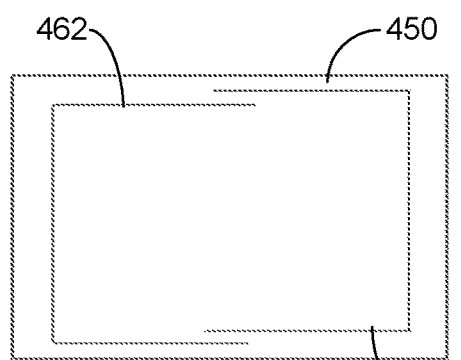
Figure 30H:
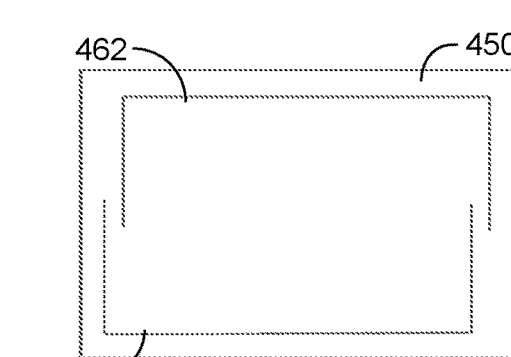
Figure 30I:
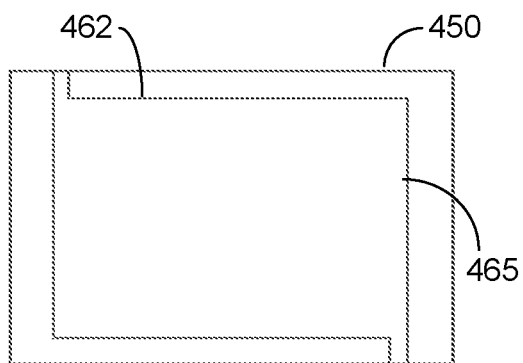
Figure 30J:
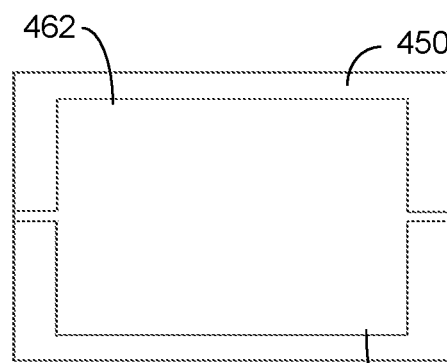
Figure 30K:
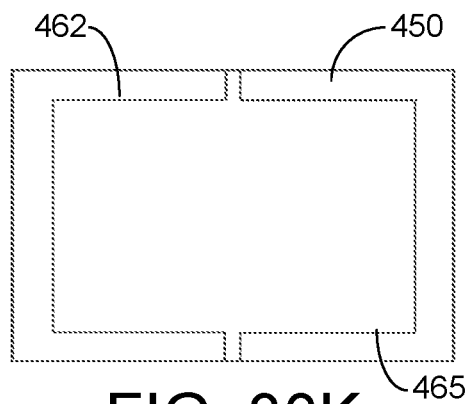
Figure 30L:
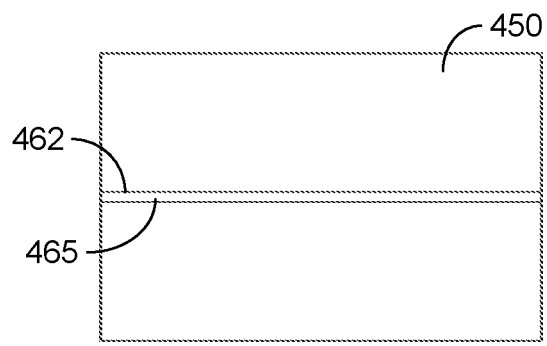
Figure 30M:
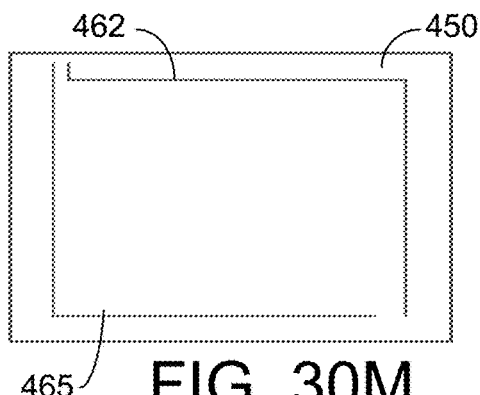
Figure 30N:
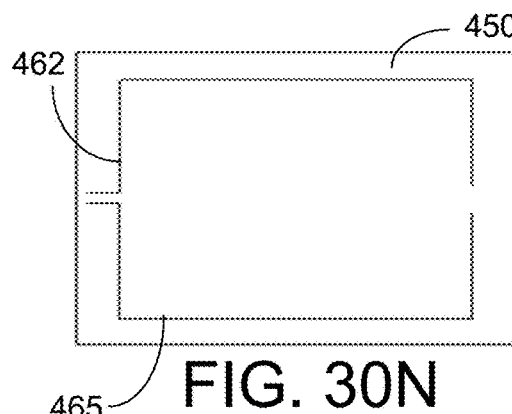
Figure 30O:
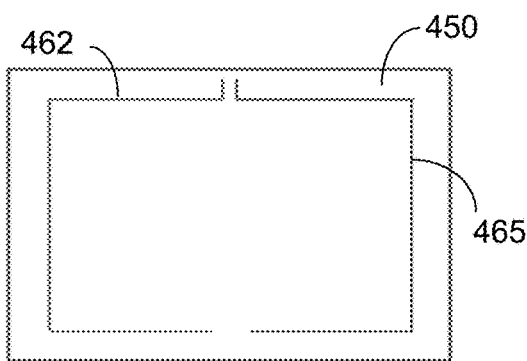
Figure 30P:
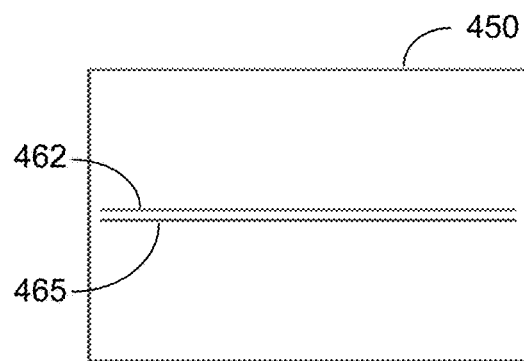
Figure 30Q:
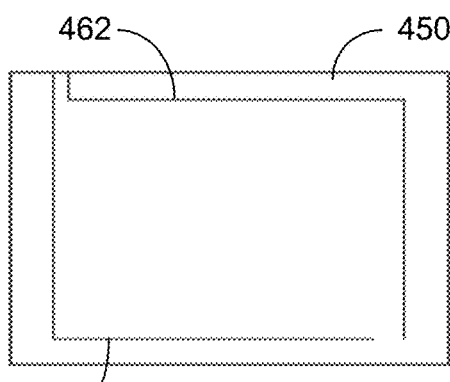
Figure 30R:
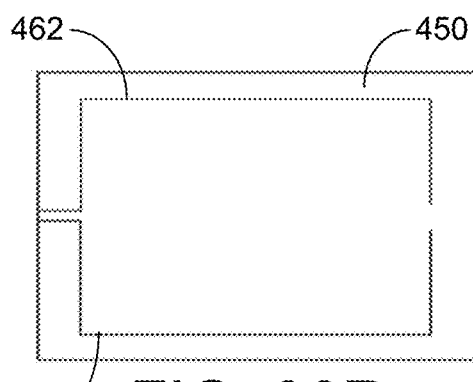
Figure 30S:
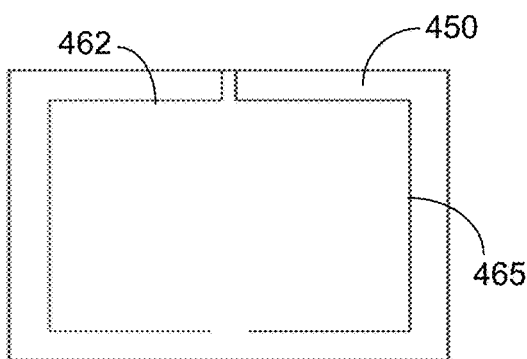
Figure 30T:
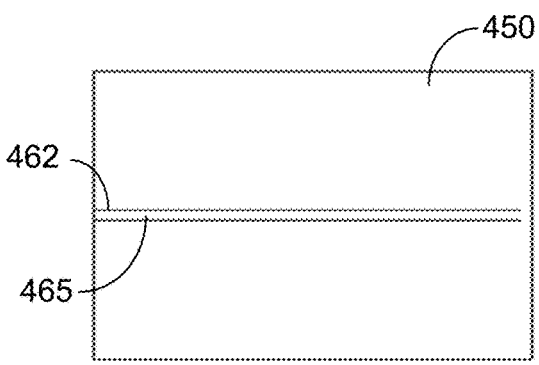

FIGS. 30A-30T show various examples of different configurations for conductive buses 462 and 465. In FIGS. 30A-30H, the conductive buses 462 and 465 do not extend to the edge of the substrate 450 whereas in FIGS. 30I-30L, the conductive buses 462 and 465 extend to the edge of the substrate 450. In FIGS. 30M-30P, the conductive buses 462 and 465 do not extend to the edge of the substrate 450 and only form one terminal end to which to connect the electronics modules 130, 470, 470'. FIGS. 30Q-30T are similar to FIGS. 30M-30P except that the conductive buses 462 and 465 extend to the edge of the substrate 450.

Figure 31A:
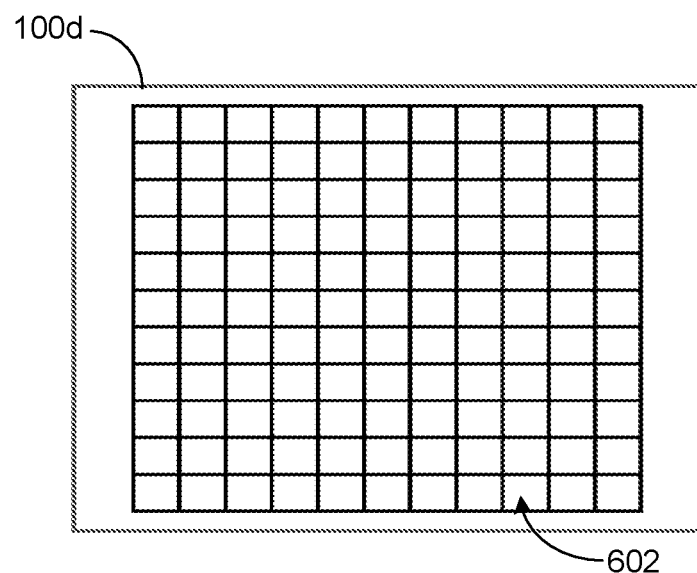
FIGS. 31A and 31B show two examples of grid marks that may be printed on the incontinence sensor pad shown in FIG. 18B.
Figure 31B:
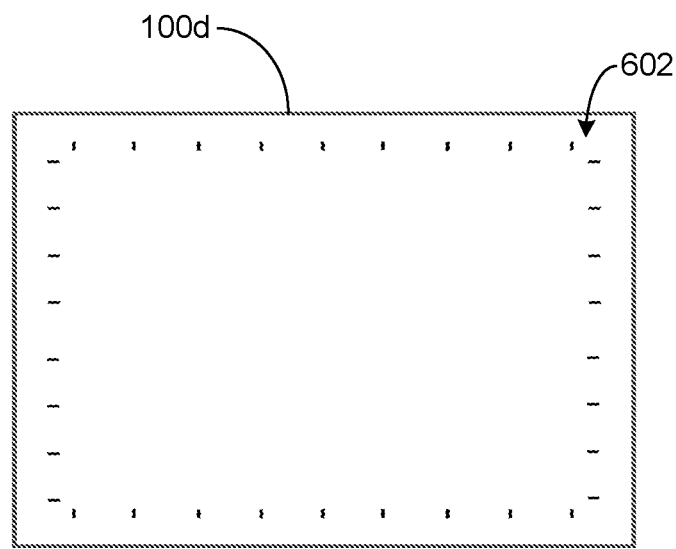

FIGS. 31A and 31B show further examples of incontinence sensor pads 100d. The incontinence sensor pad 100d may include grid markings 602 such that a caretaker can determine a relative volume of moisture that has been absorbed based upon a size of a region of the absorbent material that has expanded due to moisture absorption. The grid markings 602 make it easier for the caretaker to determine the size of the expanded region.

The absorbent material optionally includes a color change material that changes color in response to moisture absorbed such that a caretaker can determine a relative volume of moisture that has been absorbed based upon a size of the absorbent material that has changed color. The color change material may also change color in response to a pH level of a patient's skin. Such a pH indicator may show one color if the pH level is above a predetermined level, and may show a different color if the pH level is below a predetermined level.

Although the above embodiments show incontinence sensor pads 100d and 100d' configured as a flat pad, it may be configured as a diaper as disclosed in U.S. Patent Application Publication No. US 2017/0236398 A1 entitled "PATIENT MOVEMENT AND INCONTINENCE NOTIFICATION DEVICES," filed on Feb. 17, 2017, by Patrick E. Eddy et al., the entire disclosure of which is incorporated herein by reference.

Controller 70 of monitor 15 may be configured to perform a factory reset. For example, the controller 70 may be configured to reset to a factor preset condition in response to simultaneous activation of at least two of the plurality of inputs by the patient caregiver. In this case each of the sensor pads would need to be re-paired with monitor 15 and voice commands may need to be re-recorded for a patient without erasing any pre-stored tones. Such a factory reset may be desirable when a new patient replaces a prior patient in a particular room.

Controller 70 of monitor 15 may also be configured to cancel all previously paired sensor pads (but not the connected nurse call) upon pressing two buttons at once. In this case, monitor 15 is unpaired with all of the pads and those pads can no longer be re-paired with the monitor 15. This is also useful when a new patient is introduced into a room and does not require re-pairing of the nurse call. It may be possible in the alternative to configure the monitor 15 to allow the pads to be re-paired as if they were new pads.

It may also be desirable to configure controller 70 to cancel all pads and further to change the ID number of the monitor. The controller 70 may be configured to essentially perform a factory reset and change its ID number stored in memory and subsequently in the electronic key 300. This may be done in response to pressing three buttons at once on the monitor 15 (or any other means).

It is also possible to configure controller 70 to respond to user input of some sort to change the volume of the voice audio output or tones. For example, pressing of a button or combination of buttons on monitor 15 may toggle between decibel levels 71 and 91 dB.

Further, controller 70 may respond to user input of some sort to turn a night light on and off. This may be illuminator lights 84 or the light strip(s) 250.

The controller of monitor 15 and/or nurse call relay device 200 may be configured to monitor the remaining battery life of their respective batteries and to generate a warning signal when the battery is about to expire. The warning may be audibly announced or may be transmitted to the nursing station 4.

Pressure sensor pads 100a, 100b, and 100c may be constructed in any manner previously known in the art. Examples of the pressure sensor pad constructions are disclosed in U.S. Patent Application Publication No. US 2014/0221876 A1. Also, a pressure sensor pad 100 having multi-zone sensing capabilities as disclosed in U.S. Patent Application Publication No. US 2017/0236398 A1 may be used. The entire disclosures of U.S. Patent Application Publication Nos. US 2014/0221876 A1 and US 2017/0236398 A1 are incorporated herein by reference.

Conductive tracings similar to those described above for incontinence sensor pad 100d may be provided on the upper surface of a bed pressure sensor pad 100a such that the functions of the bed pressure sensor pad 100a and the incontinence sensor pad 100d may be combined into one sensor pad 100. Further, an absorbent chuck may be combined with sensor pad 100 in the same manner as discussed above and in U.S. Patent Application Publication No. US 2017/0236398 A1, the entire disclosure of which is incorporated herein by reference.

The monitor 15 may be reusable or may be disposable as described in U.S. Patent Application Publication No. US 2014/0221876 A1, the entire disclosure of which is incorporated herein by reference.

The toilet sensor 100c may be placed on a toilet to notify a caretaker that the patient has attempted to get up from the toilet on their own. A sensor for such a toilet application may be constructed using a flexible circuit that may be connected and adhered to a surface of the toilet that will contact the patient's skin. The device would thus sense the properties of human skin or pressure. The unit activates once pressure is applied to the sensor or the patient touches the flex circuit contacts. The toilet sensor 100c may be a pressure sensing pad similar to the bed and chair pad.

It may also be desirable to provide a seat belt 100e (FIG. 2) for the toilet. In this case, it may not be necessary to use a toilet pressure sensor pad 100c to detect if the patient is attempting to get up from the toilet. Instead, a seat belt clip sensor 502, which may be constructed similar to a car seat belt sensor, may be provided in the seat belt to generate a signal when the seat belt is not clipped. This signal could be transmitted by wire or wirelessly to monitor 15. If sent wirelessly, the same pairing and signal format could be used as is described above with respect to the toilet pressure sensor 100c. Thus, a patient movement notification system may include a toilet seat belt 100e for securing a patient to a toilet. The toilet seat belt 100e includes a releasable clip 504 connecting two portions of the seat belt to secure the patient, and a clip sensor 502 for sensing whether the releasable clip is clipped. The patient movement notification system may further include a signal generator 505 for generating an alarm signal when the clip sensor detects that the releasable clip is no longer clipped. Although a toilet pressure sensor pad 100c may not be needed, it may still be desirable to use it in combination with the seat belt 100e so that the signal generator only generates the alarm signal when the pressure sensor senses pressure on the toilet seat and the clip sensor 502 detects that that the releasable clip 504 is no longer connecting the two portions of the toilet seat belt 100e. The signal generator 505 may be a transmitter circuit for wirelessly transmitting the alarm signal to the monitor 15.

The patient movement notification system 10 may further include a motion sensor 600 (FIG. 2) in communication with the monitor 15 for detecting movement of the patient. The monitor 15 may track a time period from the last detected movement and generate a notification of non-movement if the motion sensor 600 does not detect movement of the patient for at least a threshold time period. This can assist the caregivers in ensuring that the patient does not develop bed sores from lack of movement. Thus, upon receiving a notification of non-movement, the caregivers can enter the room and move the patient. The motion sensor 600 may be mounted anywhere so long as it can detect movement of the patient. The motion sensor 600 may be mounted in pressure sensor pad 100a, incontinence sensor pad 100d, or monitor 15, or may be mounted separately.

The outer surfaces of housing 20 of monitor 15 and the sensor pads 100 are preferably treated with an antimicrobial substance. The surfaces of housing 20 and sensor pads 100 may be coated with an antimicrobial treatment that may be sprayed onto the surfaces using a solution and/or may be applied using wipes soaked in such a solution. Suitable wipes and solutions are disclosed in commonly assigned U.S. Pat. No. 8,491,922, the entire disclosure of which is incorporated herein by reference. The above-noted surfaces may also be treated with a mixture of 3-(trihydroxysilyl) propyldimethyloctadecyl ammonium chloride and hydrogen peroxide.

Various aspects of the above embodiments may be integrated into a bed. For example, the bed pressure sensor pad 100a may be integrated into a bed mattress. An example of such is disclosed in U.S. Patent Application Publication No. US 2017/0236398 A1, the entire disclosure of which is incorporated herein by reference. In this case, the bed 5 may include an electronic interface to connect the integrated bed pressure sensor pad 100a to the monitor 15 via wired or wireless connection, and an absorbent chuck and incontinence sensor may be provided on top of the mattress and may be connected to the electronic interface included in the bed so that a monitor 15 or alarm interface may be used.

By providing microphone 60 and voice recognition capabilities in monitor 15, the monitor 15 may be programmed to respond to voice commands in a manner similar to how an Amazon Echo®, Apple HomePod®, or Google Home® operates.

As used herein, the term "communicatively coupled" means that two components are associated and configured so that they communicate with one another. Such communicative coupling may be provided by hardwiring the devices or by providing for wireless communication therebetween.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by any subsequently presented claims as interpreted according to the principles of patent law, including the doctrine of equivalents.

What is claimed is:

1. A patient movement notification system, comprising:
a first sensor pad comprising a pressure sensor for sensing pressure applied by a patient, and a transmitter circuit for transmitting first wireless signals;
a second sensor pad comprising a pressure sensor for sensing pressure applied by a patient, and a transmitter circuit for transmitting second wireless signals; and
a monitor having a receiver for receiving the first and second wireless signals, the monitor generating a notification of patient movement in response to one of the first and second wireless signals,
wherein the second sensor pad is a different type of sensor pad from said first sensor pad, and wherein the first and second wireless signals include a type code that identifies the type of sensor pad from which the first and second wireless signals are sent,
wherein all sensor pads of the same type have the same type code, and
wherein the monitor determines from the first and second wireless signals whether one of the sensor pads sensed pressure and subsequently did not sense pressure and responds by generating notification of patient movement; and
wherein the patient movement notification system further comprising a nurse call relay device having a nurse call receiver for receiving signals from a transmitter of the monitor and a transmitter for transmitting signals to the receiver of the monitor,
wherein the signals sent from the nurse call relay device include a type code that identifies the signals as coming from the nurse call relay device; and
wherein the monitor is configured to respond to wireless signals from only one nurse call relay device.

2. The patient movement notification system of claim 1, wherein the first and second wireless signals include an active code that identifies whether the sensor pad from which the first and second wireless signals are sent is active.

3. The patient movement notification system of claim 2, wherein only one of the first and second sensor pads is active at any time.

4. A patient movement notification system comprising:
a first sensor pad comprising a pressure sensor for sensing pressure applied by a patient, and a transmitter circuit for transmitting first wireless signals;
a second sensor pad comprising a pressure sensor for sensing pressure applied by a patient, and a transmitter circuit for transmitting second wireless signals; and
a monitor having a receiver for receiving the first and second wireless signals, the monitor generating a notification of patient movement in response to one of the first and second wireless signals, wherein the second sensor pad is a different type of sensor pad from said first sensor pad, and wherein the first and second wireless signals include a type code that identifies the type of sensor pad from which the first and second wireless signals are sent,
wherein the monitor is configured to respond to wireless signals from only one sensor pad of a particular type.

5. The patient movement notification system of claim 4, wherein the monitor is configured to respond to wireless signals from only one sensor pad of a bed type, and only one sensor pad of a chair type, and only one sensor pad of a toilet type.

6. The patient movement notification system of claim 1, wherein the first sensor pad is a bed type sensor pad, and the second sensor pad is one of a chair type sensor pad and a toilet type sensor pad.

7. The patient movement notification system of claim 1 and further comprising
a third sensor pad comprising an incontinence sensor for sensing moisture due to incontinence, and a transmitter associated with the third sensor pad for transmitting third wireless signals in response to the incontinence sensor,
wherein the receiver receives the third wireless signals and the monitor generates a notification of incontinence in response to the third wireless signals, and
wherein the third wireless signals include a type code that identifies the type of sensor pad from which the third wireless signals are sent.

8. A patient movement notification system comprising:
a first sensor pad comprising a pressure sensor for sensing pressure applied by a patient, and a transmitter circuit for transmitting first wireless signals;
a second sensor pad comprising a pressure sensor for sensing pressure applied by a patient, and a transmitter circuit for transmitting second wireless signals;
a monitor having a receiver for receiving the first and second wireless signals, the monitor generating a notification of patient movement in response to one of the first and second wireless signals,
wherein the second sensor pad is a different type of sensor pad from said first sensor pad, and
wherein the first and second wireless signals include a type code that identifies the type of sensor pad from which the first and second wireless signals are sent;
a toilet seat belt for securing a patient to a toilet, the toilet seat belt comprising:
a releasable clip connecting two portions of the seat belt to secure the patient; and
a clip sensor for sensing whether the releasable clip is connecting the two portions of the seat belt; and
a signal generator for transmitting an alarm signal to the monitor when the clip sensor detects that the releasable clip no longer senses that the releasable clip is connecting the two portions of the seat belt; and
a signal generator for transmitting an alarm signal to the monitor when the clip sensor detects that the releasable clip no longer senses that the releasable clip is connecting the two portions of the seat belt;
wherein the monitor is configured to respond to wireless signals from only one toilet seat belt.

9. A patient movement notification system, comprising:
a first sensor pad comprising a pressure sensor for sensing pressure applied by a patient, and a transmitter circuit for transmitting first wireless signals;
a second sensor pad comprising a pressure sensor for sensing pressure applied by a patient, and a transmitter circuit for transmitting second wireless signals; and
a monitor having a receiver for receiving the first and second wireless signals, the monitor generating a notification of patient movement in response to one of the first and second wireless signals,
wherein the first and second wireless signals include an active code that identifies whether the sensor pad from which the first and second wireless signals are sent is either sensing pressure applied to the sensor pad or not sensing pressure, and wherein the monitor determines from the first and second wireless signals whether one of the sensor pads sensed pressure and subsequently did not sense pressure and responds by generating notification of patient movement; and
wherein the monitor is configured to respond to wireless signals from only one sensor pad of a particular type.

10. The patient movement notification system of claim 9, and further comprising a third sensor pad comprising an incontinence sensor for sensing moisture due to incontinence, and a transmitter associated with the third sensor pad for transmitting third wireless signals in response to the incontinence sensor,
wherein the receiver receives the third wireless signals and the monitor generates a notification of incontinence in response to the third wireless signals.

11. The patient movement notification system of claim 10, wherein the first, second, and third wireless signals include a type code that identifies the type of sensor pad from which the signals are sent, wherein all sensor pads of the same type have the same type code.

12. The patient movement notification system of claim 9, wherein the first, second, and third wireless signals include a type code that identifies the type of sensor pad from which the signals are sent, wherein all sensor pads of the same type have the same type code.

13. The patient movement notification system of claim 9, and further comprising a nurse call relay device having a nurse call receiver for receiving signals from a transmitter of the monitor, and a transmitter for transmitting signals to the receiver of the monitor, wherein the signals sent from the nurse call relay device include a type code that identifies the signals as coming from the nurse call relay device.

* * * * *